United States Patent [19]
Bao et al.

[11] Patent Number: 6,051,590
[45] Date of Patent: Apr. 18, 2000

[54] IMMUNOSUPPRESSANT TRICYCLIC COMPOUNDS

[75] Inventors: Jianming Bao, Scotch Plains; Frank Kayser, Hoboken; Robert K. Baker, Cranford; Shouwu Miao, Edison; William H. Parsons, Belle Mead; Kathleen M. Rupprecht, Cranford, all of N.J.

[73] Assignee: Merck & Co., Inc., Rahway, N.J.

[21] Appl. No.: 09/311,518

[22] Filed: May 13, 1999

[51] Int. Cl.[7] ............... A61K 31/336; A61K 31/357; C07D 319/00; C07D 303/04
[52] U.S. Cl. ............... 514/376; 514/452; 514/475; 514/510; 514/512; 514/557; 514/579; 514/719; 549/358; 560/7; 560/147; 560/156; 560/179; 562/404; 562/498; 562/507
[58] Field of Search ............... 514/376, 452, 514/475, 510, 512, 557, 579, 719; 549/358; 560/7, 147, 179, 156; 562/404, 498, 507

[56] References Cited

U.S. PATENT DOCUMENTS

| | | |
|---|---|---|
| 3,483,191 | 12/1969 | Krakower et al. |
| 3,869,506 | 3/1975 | Shen et al. |
| 4,434,073 | 2/1984 | Sucrow et al. |
| 4,453,967 | 6/1984 | Mori . |
| 5,010,104 | 4/1991 | Oshima et al. |
| 5,599,950 | 2/1997 | Teng . |
| 5,631,282 | 5/1997 | Goetz . |
| 5,679,705 | 10/1997 | Baker et al. |
| 5,696,156 | 12/1997 | Baker et al. |
| 5,763,478 | 6/1998 | Baker et al. |
| 5,874,594 | 2/1999 | Baker et al. |
| 5,883,119 | 3/1999 | Baker et al. |
| 5,952,371 | 9/1999 | Baker et al. |

FOREIGN PATENT DOCUMENTS

| | | |
|---|---|---|
| WO 96/40688 | 12/1996 | WIPO . |
| WO 97/16068 | 5/1997 | WIPO . |
| WO 97/16182 | 5/1997 | WIPO . |
| WO 97/16437 | 5/1997 | WIPO . |
| WO 97/16438 | 5/1997 | WIPO . |
| WO98/16532 | 4/1998 | WIPO . |

OTHER PUBLICATIONS

Abad et al: J. Chem. Soc., Perkin Trans., 1(17) pp. 2193–2199, 1996.
Phytochemistry, vol. 29, No. 7 pp. 2257–2261 (1990), by Abreu, et al.
J. Org. Chem, vol. 32, pp. 1875–1877 (1967), by Sabata, et al.

*Primary Examiner*—Johann Richter
*Assistant Examiner*—Taofiq A Solola
*Attorney, Agent, or Firm*—J. Antonio Garcia-Rivas; Mark R. Daniel

[57] ABSTRACT

The compounds of Formula I are useful as immunosuppressive agents.

16 Claims, No Drawings

IMMUNOSUPPRESSANT TRICYCLIC COMPOUNDS

BACKGROUND OF THE INVENTION

The present invention relates to a class of tricyclic compounds that are useful as potassium channel inhibitors to treat autoimmune disorders and the like.

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates. Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A (CsA), which was approved by the US FDA in 1983 is currently the leading drug used to prevent rejection of transplanted organs. In 1993, FK-506 (Prograf) was approved by the US FDA for the prevention of rejection in liver transplantation. CsA and FK-506 act by inhibiting the body's immune system from mobilizing its vast arsenal of natural protecting agents to reject the transplant's foreign protein. In 1994, CsA was approved by the US FDA for the treatment of severe psoriasis and has been approved by European regulatory agencies for the treatment of atopic dermatitis. Though they are effective in fighting transplant rejection, CsA and FK-506 are known to cause several undesirable side effects including nephrotoxicity, neurotoxicity, and gastrointestinal discomfort. Therefore, a selective immunossuppressant without these side effects still remains to be developed. Potassium channel inhibitors promise to be the solution to this problem.

The importance of potassium channels was first recognized almost fifty years ago when Hodgkin and Huxley discovered that potassium ions contributed to the current that excited the squid giant. Research in the area, however, was hampered by the lack of selective, high affinity ligands for potassium channels. But the advent of recombinant DNA techniques and single cell and whole cell voltage clamp techniques has changed the slow pace of the field. Potassium channels have turned out to be the most diverse family of ion channels discovered to date. They modulate a number of cellular events such as muscle contraction, neuro-endocrine secretion, frequency and duration of action potentials, electrolyte homeostasis, and resting membrane potential.

Potassium ion channels have been classified according to their biophysical and pharmacological characteristics.

Salient among these are the voltage dependent potassium channels, such as $K_v1$. The $K_v1$ class of potassium channels is further subdivided depending on the function of the channel, for example $K_v1.1$, $K_v1.3$, $K_v1.5$. Functional voltage-gated $K^+$ channels can exist as multimeric structures formed by the association of either identical or dissimilar subunits. This phenomena is thought to account for the wide diversity of $K^+$ channels. However, subunit compositions of native $K^+$ channels and the physiologic role that particular channels play are, in most cases, still unclear.

Membrane depolarization by $K_v1.3$ inhibition has been shown to be an effective method to prevent T-cell proliferation and therefore has applications in many autoimmune conditions. Inhibition of $K^+$ channels in the plasma membrane of human T-lymphocytes has been postulated to play a role in eliciting immunosuppressive responses by regulating intracellular $Ca^{++}$ homeostasis, which has been found to be important in T-cell activation.

The $K_v1.3$ voltage-gated potassium channel is found in neurons, blood cells, osteoclasts and T-lymphocytes. The Chandy and Cahalan laboratories proposed a hypothesis that blocking the $K_v1.3$ channel would elicit an immunosuppressant response. (Chandy et al., *J. Exp. Med.* 160, 369, 1984; Decoursey et al., Nature, 307, 465, 1984). However, the K+ channel blockers employed in their studies were nonselective. Until research with the peptide margatoxin, a peptide found in scorpion venom, no specific inhibitor of the $K_v1.3$ channel existed to test this hypothesis. Although a laboratory (Price et al., *Proc. Natl. Acad. Sci. USA*, 86, 10171, 1989) showed that charybdotoxin would block $K_v1.3$ in human T cells, charybdotoxin was subsequently shown to inhibit four different $K^+$ channels ($K_v1.3$ and three distinct small conductance $Ca^{++}$ activated $K^+$ channels) in human T-lymphocytes, limiting the use of this toxin as a probe for the physiological role of $K_v1.3$ (Leonard et al., *Proc. Natl. Acad. Sci. USA*, 89, 10094, 1992). Margatoxin, on the other hand, blocks only $K_v1.3$ in T-cells, and has immunosuppressant activity in both in vitro and in vivo models. (fin et al., *J. Exp. Med,* 177, 637, 1993). The therapeutic utility of this compound, however, is limited by its potent toxicity. Recently, a class of compounds have been reported that may be an attractive alternative to the above-mentioned drugs, see for example U.S. Pat. Nos. 5,670,504; 5,631,282; 5,696, 156; 5,679,705; and 5,696,156. While addressing some of the activity/toxicity problems of previous drugs, there is still a need to develop other compounds that would offer alternative treatments with differing toxicity profiles and patient tolerability.

Four active components of *Spachea correa* were recently identified which inhibit thymidine uptake of T cells. U.S. Pat. No. 5,631,282.

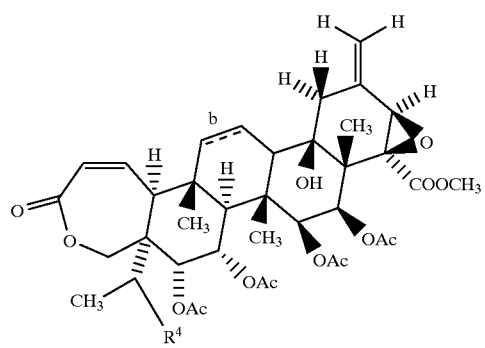

-continued

Formula 1(a) b is a single bond and $R^4$ is OAc
Formula 1(b) b is a double bond and $R^4$ is OAc
Formula 1(c) b is a single bond and $R^4$ is OH
Formula 1(d) b is a double bond and $R^4$ is OH These compounds are useful as immunosuppressive agents in animals, including man. The present invention describes newly developed immunosuppressive compounds derived from the compounds described in Formulae 1(a) through 1(d) and which have the relative stereochemistry depicted above.

SUMMARY OF THE INVENTION

This invention relates to a class of triterpene derivatives of the general structural Formula I

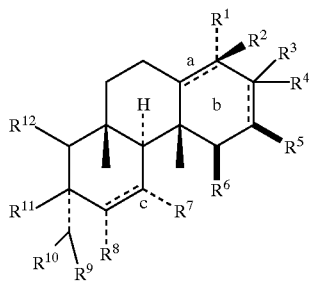

are useful as immunosuppressives.

As an immunosuppressive, the compounds of this invention are useful in the treatment of autoimmune diseases, the prevention of rejection of foreign organ transplants and/or related afflictions, diseases and illnesses. Also within the scope of this invention are pharmaceutical formulations comprising a compound of Formula I and a pharmaceutical carrier, as well as, pharmaceutical formulations comprising a compound of Formula I, and one or more immunosuppressive compounds and a pharmaceutical carrier.

DETAILED DESCRIPTION OF THE INVENTION

A. Scope of the Invention

The present invention is related to compounds of Formula I, including but not limited to those specified in the examples, which are useful in a mammalian subject for the treatment and prevention of the resistance by transplantation of organs or tissue, graft-versus-host diseases brought about by medulla ossium transplantation; rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, bronchial asthma, allergic asthma, intrinsic asthma, extrinsic asthma and dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth; muscular dystrophy; Pyoderma and Sezary's syndrome, Addison's disease, ischemia-reperfusion injury of organs which occurs upon preservation, transplantation or ischemic disease, for example, thrombosis and cardiac infraction, endotoxin-shock, pseudomembranous colitis, colitis caused by drug or radiation, ischemic acute renal insufficiency, chronic renal insufficiency, toxinosis caused by lung-oxygen or drug, for example, paracort and bleomycins, lung cancer, pulmonary emphysema, cataracta, siderosis, retinitis, pigmentosa, senile macular degeneration, vitreal scarring, corneal alkali burn; dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy; disease caused by histamine or leukotriene-$C_4$ release; Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmention of chemotherapeutic effect, preventing or treating activity of cytomegalovirus infection, HCMV infection, and antiinflammatory activity; and treatment of immunodepression or a disorder involving immunodepression, including AIDS, cancer, senile dementia, trauma, chronic bacterial infection, and certain central nervous system disorders.

More particularly, this invention relates to compounds of the general structural Formula I:

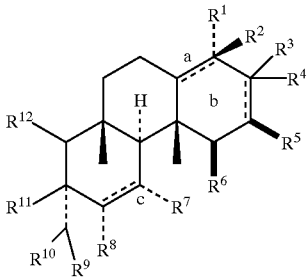

or a pharmaceutically acceptable salt, crystal form or hydrate thereof, wherein a, b and c are independently a single bond or a double bond, and represented by === in the structure above;
n is: 0, 1 or 2;
r is: 0 or 1;
s is: 0 or 1;
$R^1$ and $R^2$ are independently:
(1) hydroxyl,
(2) $(C_1-C_6)$-alkyloxy,
(3) H,
(4) $OCO(C_1-C_6)$-alkyl,
(5) $(C_1-C_6)$-alkyl,
(6) $R^1$ and $R^2$ taken together is an exo-methylene group,
(7) $R^1$ and $R^2$ taken together is =O,
(8) $(C_1-C_6)$-alkylaryl, wherein aryl is as defined in $R^{11}$ below, or
(9) $(C_2-C_8)$alkenyl;
with the proviso that $R^2$ is absent when a is a double bond;
$R^3$ and $R^4$ are independently:
(1) hydroxyl,
(2) $(C_1-C_6)$-alkyloxy,
(3) H,
(4) $OCO(C_1-C_6)$-alkyl,
(5) $(C_1-C_6)$-alkyl,
(6) phenyl,
(7) $R^3$ and $R^5$ taken together is an oxirane group when b is a single bond, or
(8) $(CH_2)_n$aryl, wherein aryl is as defined below;
with the proviso that $R^4$ is absent when b is a double bond, additionally, $R^3$ and $R^4$ can be taken together to be =O when b is a single bond;
$R^5, R^6, R^7$ and $R^8$ are independently selected from the group consisting of:
(1) $O[(C=O)O_r]_sR^{13}$,
(2) $O[(C=O)O_r]_s$-aryl, aryl as defined below,
(3) $O[(C=O)O_r]_s$-heteroaryl,
(4) hydrogen,
(5) $(C_1-C_6)$alkylaryl, wherein aryl is as defined below, and
(6) hydroxyl;
$R^9$ is:
(1) H.
(2) OH,
(3) =O,
(4) $O[(C=O)O_r]_s(C_1-C_6)$-alkyl, alkyl as defined below,
(5) $O[(C=O)O_r]_s(C_2-C_6)$-alkenyl, as defined below,
(6) $O[(C=O)O_r]_s$-aryl, aryl as defined below,
(7) $O[(C=O)O_r]_s$-heteroaryl,
(8) $O(CH_2)_n$-heteroaryl,
(9) $O(CH_2)_n$-aryl, aryl as defined below, or
(10) $R^9$ and $R^{12}$ are connected to form

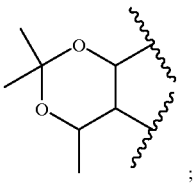

;

$R^{10}$ is:
(1) $CH_3$, or
(2) H;
$R^{11}$ is chosen from the group consisting of:
(1) H,
(2) $(C_1-C_6)$-alkyl, wherein alkyl is unsubstituted or substituted with one or two of the substituents selected from the group consisting of:
(a) halo, wherein halo is fluoro, chloro, bromo, or iodo,
(b) hydroxy,
(c) oxo,
(d) $(C_1-C_6)$-alkyloxy,
(e) $(C_1-C_6)$-alkyl—$S(O)_n$—,
(f) aryl-$(C_1-C_6)$-alkyloxy, wherein aryl is defined as phenyl or naphthyl, unsubstituted or substituted with one, two or three of the substituents selected from the group consisting of:
(a') halo, wherein halo is fluoro, chloro, bromo, or iodo,
(b') hydroxy,
(c') $(C_1-C_6)$-alkyl,
(d') $(C_1-C_4)$-perfluoroalkyl,
(e') $(C_1-C_6)$-alkenyl,
(f') $(C_1-C_6)$-alkynyl,
(g') $(C 1-C_6)$-alkyloxy,
(h') $(C_1-C_6)$-alkyl—$S(O)_n$—,
(i') phenyl,
(j') phenoxy,
(k') cyano,
(l') nitro,
(m') $CO_2H$,
(n') $CO(C_1-C_6)$-alkyl,
(o') $CO_2(C_1-C_6)$-alkyl,
(p') $CONR^{13}R^{14}$,
(q') $NR^{13}R^4$,
(r') $NR^{13}CO(C_1-C_6)$-alkyl,
(s') $(C_1-C_6)$-alkenyloxy, and
(t') benzyloxy;
(g) cyano,
(h) nitro,
(i) vinyl,
(j) $NR^{13}R^{14}$,
(k) $NR^{13}CO(C_1-C_6)$-alkyl,
(l) CHO,
(m) $CO_2H$,
(n) $CO(C_1-C_6)$-alkyl,
(o) $CO_2(C_1-C_6)$-alkyl,
(p) $CONR^{13}R^{14}$,
(q) aryl, wherein aryl is as defined above,
(r) $OCOCH_3$, and
(s) $(CH_2)_nO(CO)CHSPh_2$;
(3) $(C_2-C_6)$-alkenyl, wherein alkenyl is unsubstituted or substituted with one or two of the substituents selected from the group consisting of:

(a) halo, wherein halo is fluoro, chloro, bromo, or iodo,
(b) hydroxy,
(c) oxo,
(d) $(C_1-C_6)$-alkyloxy,
(e) $(C_1-C_6)$-alkyl—$S(O)_n$—,
(f) phenyl-$(C_1-C_6)$-alkyloxy,
(g) cyano,
(h) nitro,
(i) vinyl,
(j) $NR^{13}R^{14}$,
(k) $NR^{13}CO(C_1-C_6)$-alkyl,
(l) CHO,
(m) $CO_2H$,
(n) $CO(C_1-C_6)$-alkyl,
(o) $CO_2(C_1-C_6)$-alkyl,
(p) $CONR^{13}R^{14}$,
(q) aryl, wherein aryl is as defined above,
(r) heteroaryl, and
(s) $OCOCHC_3$,
(4) $(CH_2)_nO(C_2-C_6)$-alkenyl, wherein alkenyl is as defined above,
(5) CHO,
(6) COOH,
(7) $CONR^{13}R^{14}$,
(8) $O[(C=O)O_r]_s(C_1-C_6)$-alkyl, alkyl as defined above,
(9) $(CH_2)_nS(C_1-C_6)$-alkyl, wherein alkyl is as defined above,
(10) $(CH_2)_nS(C_2-C_6)$-alkenyl, wherein alkenyl is as defined above,
(11) $(CH_2)_nS$-aryl, wherein aryl is as defined above, or
(12) $(CO)(C_1-C_6)$-alkyl, wherein alkyl is as defined above;

$R^{12}$ is as defined above for $R^{11}$ or
(1) =O,
(2) =CH—$(C_1-C_6)$-alkyl, wherein alkyl is as defined above,
(3) =CH—$(C_1-C_6)$-alkenyl, wherein alkenyl is as defined above,
(4) =CH-aryl, wherein aryl is as defined above,
(5) hydroxyl, or
(6) $R^9$ and $R^{12}$ are connected to form

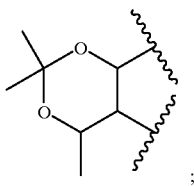
;

$R^{13}$ and $R^{14}$ are independently:
(1) hydrogen,
(2) $(C_1-C_6)$-alkyl, or
(3) phenyl.

A more preferred embodiment is the compound of structural Formula I as recited above wherein:
$R^1$ and $R^2$ are independently:
(1) hydroxyl,
(2) $(C_1-C_6)$-alkyloxy,
(3) H,
(4) $(C_1-C_6)$-alkyl,
(5) $R^1$ and $R^2$ taken together is =O,
(6) $(C_1-C_6)$-alkylbenzene wherein the benzene is unsubstituted or substituted with $(C_1-C_6)$alkyloxy, hydroxyl, or $(C_1-C_6)$alkyl, and alkyl is branched or unbranched, or
(7) $(C_2-C_8)$alkenyl;

with the proviso that $R^2$ is absent when a is a double bond;
$R^3$ and $R^4$ are independently:
(1) hydroxyl,
(2) $(C_1-C_6)$-alkyloxy,
(3) H,
(4) $OCO(C_1-C_6)$-alkyl,
(5) $(C_1-C_6)$-alkyl,
(6) phenyl,
(7) $R^3$ and $R^5$ taken together is an oxirane group when b is a single bond, or
(8) $(CH_2)_n$benzene, wherein the benzene is unsubstituted or substituted with hydroxyl or $(C_1-C_6)$-alkyloxy;

with the proviso that $R^4$ is absent when b is a double bond, additionally, $R^3$ and $R^4$ can be taken together to be =O when b is a single bond;
$R^5$, $R^6$, $R^7$ and $R^8$ are independently selected from the group consisting of:
(1) $O[(C=O)O_r]_sR^{13}$,
(2) $O[(C=O)O_r]_s$-aryl,
(3) hydrogen,
(4) $(C_1-C_6)$alkylbenzene, wherein the benzene is unsubstituted or substituted with $(C_1-C_6)$-alkyl and alkyl is branched or unbranched;
(5) hydroxyl;

$R^9$ is:
(1) H,
(2) OH,
(3) =O,
(4) $O[(C=O)O_r]_s(C_1-C_6)$-alkyl, wherein alkyl is branched or unbranched, or
(5) $R^9$ and $R^{12}$ are connected to form

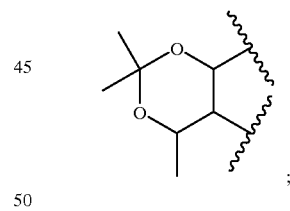
;

$R^{10}$ is:
(1) $CH_3$, or
(2) H;

$R^{11}$ is chosen from the group consisting of:
(1) H,
(2) $(CH_2)_nO(CO)CH(SPh)_2$,
(3) $(CH_2)_nO(C_1-C_6)$alkyl,
(4) $(CO)(C_1-C_6)$-alkyl,
(5) $(C_1-C_6)$-alkyl, or
(6) CHO;

$R^{12}$ is as defined above for $R^{11}$ or
(1) =O,
(2) $O(CO)(C_1-C_6)$-alkyl,
(3) hydroxyl, or (4) $R^9$ and $R^{12}$ are connected to form

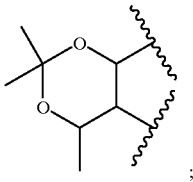

;

$R^{13}$ is:
(1) hydrogen, or
(2) $(C_1-C_6)$-alkyl.

Another preferred embodiment is the compound of structural Formula I as recited above, wherein
$R^1$ and $R^2$ are independently:
(1) hydroxyl,
(2) H,
(3) $R^1$ and $R^2$ taken together is =O,
(4) $(C_1-C_3)$-alkylbenzene wherein the benzene is unsubstituted or substituted with $(C_1-C_3)$alkyloxy, hydroxyl, or $(C_1-C_3)$alkyl, and alkyl is branched or unbranched, or
(5) $(C_2-C_8)$alkenyl;
with the proviso that $R^2$ is absent when a is a double bond;
$R^3$ and $R^4$ are independently:
(1) hydroxyl,
(2) $(C_1-C_3)$-alkyloxy,
(3) H,
(4) $(C_1-C_3)$-alkyl,
(5) $(CH_2)_n$benzene, wherein the benzene is unsubstituted or substituted with hydroxyl or $(C_1-C_3)$-alkyloxy;
with the proviso that $R^4$ is absent when b is a double bond, additionally, $R^3$ and $R^4$ can be taken together to be =O when b is a single bond;
$R^5, R^6, R^7$ and $R^8$ are independently selected from the group consisting of:
(1) $O(C=O)(C_1-C_3)$alkyl,
(2) hydrogen,
(3) $(C_1-C_3)$alkylbenzene, wherein the benzene is unsubstituted or substituted with $(C_1-C_3)$-alkyl and alkyl is branched or unbranched;
(4) $O(C_1-C_3)$alkyl, and
(5) hydroxyl;
$R^9$ is:
(1) H.
(2) OH,
(3) =O,
(4) $O(C=O)(C_1-C_3)$alkyl -alkyl, or
(5) $R^9$ and $R^{12}$ are connected to form

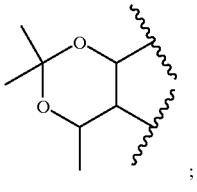

;

$R^{10}$ is:
(1) $CH_3$, or
(2) H;
$R^{11}$ is chosen from the group consisting of:
(1) H,
(2) $CH_2O(CO)CH(SPh)_2$,
(3) $CH_2O(C_1-C_3)$alkyl, and
(4) $(C_1-C_3)$-alkyl;
$R^{12}$ is:
(1) =O,
(2) $R^9$ and $R^{12}$ are connected to form

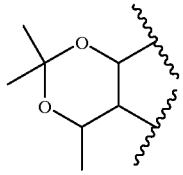

, (3) CHO,
(4) $CH_2O(C_1-C_3)$alkyl,
(5) hydroxyl, or
(6) $O(CO)(C_1-C_3)$alkyl;

A most preferred embodiment is a compound selected from the group consisting of:

1β-S-2α,2β,3α,4α,3aα,4bβ,5β,8aα,10aβ]-2α-(1-R-acetoxyethyl)-2β-(2,2-diphenylthioacetoxymethyl)-1-formyl-8-oxo-2b,4b,7,10a-tetramethyl-3,4,5-triacetoxy-1,2,3,4,4a,4b,5,8,8a,9,10,10a-dodecahydro-2-[H]-phenanthrene,

[1β-S-2α,2β,3α,4α,3aα,4bβ,5β,8aα,10aα]-2α-(1-R-acetoxyethyl)-2β-(2,2-diphenylthioacetoxymethyl)-1-formyl-8-(2-(2-methoxyphenyl)ethyl)-8-hydroxy-2b,4b,7,10a-tetramethyl-3,4,5-triacetoxy-1,2,3,4,4a,4b,5,8,8a,9,10,10a-dodecahydro-2-[H]-phenanthrene, 1β-S-2α,2β,3α,4α,3aα,4bβ,5β,8aα,10aβ]-2α-(1-R-acetoxyethyl)-1β,2β-bis(hydroxymethyl)-8-(2-(2-methoxyphenyl)ethyl)-8-hydroxy-2b,4b,7,10a-tetramethyl-3,4,5-triacetoxy-1,2,3,4,4a,4b,5,8,8a,9,10,10a-dodecahydro-2-[H]-phenanthrene, 1β-S-2α,2β,3α,4α,3aα,4bβ,5β,8aα,10aβ]-2α-(1-R-acetoxyethyl)-1β,2β-bis(methoxymethyl)-8-(2-(2-methoxyphenyl)ethyl)-8-hydroxy-2b,4b,7,10a-tetramethyl-3,4,5-triacetoxy-1,2,3,4,4a,4b,5,8,8a,9,10,10a-dodecahydro-2-[H]-phenanthrene, 4b-S-4aα,4bβ,8aα,10aβ]-2α-(1-R-acetoxyethyl)-2β-methyl-8-hydroxy-1-oxo-2,4b,7,10a-tetramethyl-1,2,4a,4b,5,6,8a,9,10,10a-decahydro-1-[H]-phenanthrene,

[1-S-3α,4α,4aα,4bβ,7β,8aα,10aβ]-2α-(1-R-acetoxyethyl)-8-(2-S-(2-ethylphenyl)propyl)-3,4-diacetoxy-1,8β-dihydroxy-2β,4b,7,10a-tetramethyl-1,2,3,4,4a,4b,5,6,7,8,8a,9,10,10a-tetradecahydro-2-[H]-phenanthrene,

[2-R-4aα,4bβ,7β,8aα,10aβ]-2α-(1-R-acetoxyethyl)-8-(2-S-(2-ethylphenyl)propyl)-8β-hydroxy-1-oxo-2β,4b,7,10a-tetramethyl-1,2,4a,4b,5,6,7,8,8a,9,10,10a-tetradecahydro-2-[H]-phenanthrene,

[1-S-3α,4α,4aα,4bβ,7β,8aα,10aβ]-2α-(1-R-hydroxyethyl)-8-(2-S-(2-ethylphenyl)propyl)-3,4-diacetoxy-1,8β-dihydroxy-2β,4b,7,10a-tetramethyl-1,2,3,4,4a,4b,5,6,7,8,8a,9,10,10a-tetradecahydro-2-[H]-phenanthrene, dimethylketal,

[1-S-3α,4α,4aα,4bβ,7β,8aα,10aβ]-2α-(1-R-acetoxyethyl)-8-(2-S-(2-ethylphenyl)propyl)-1,3,4-triacetoxy-8β-hydroxy-2β,4b,7,10a-tetramethyl-1,2,3,4,4a,4b,5,6,7,8,8a,9,10,10a-tetradecahydro-2-[H]-phenanthrene,

[1-S-3α,4α,4aα,4bβ,7β,8aα,10aβ]-2α-(1-R-acetoxyethyl)-8-(2-S-(2-ethylphenyl)propyl)-3,4-diacetoxy-1,8β-dihydroxy-2β,4b,7,10a-tetramethyl-1,2,3,4,4a,4b,5,6,7,8,8a,9,10,10a-tetradecahydro-2-[H]-phenanthrene, and

[1-S-3α,4α,4aα,4bβ,7β,8aα,10aβ]-2α-(1-R-acetoxyethyl)-8-(2-S-(2-ethylphenyl)propyl)-3,4-diacetoxy-8β-hydroxy-1-oxo-2β,4b,7,10a-tetramethyl-1,2,3,4,4a,4b,5,6,7,8,8a,9,10,10a-tetradecahydro-2-[H]-phenanthrene or a pharmaceutically acceptable salt, crystal form or hydrate thereof Another most preferred embodiment is a compound of structural Formula II.

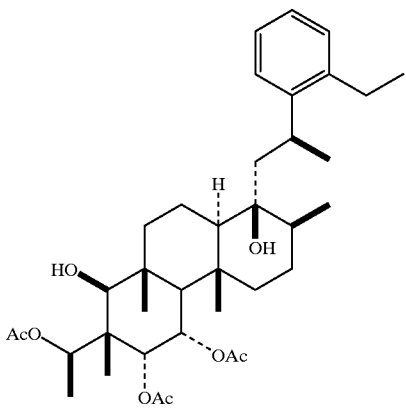

II

And yet another most preferred embodiment of the invention is a compound of structural Formula III.

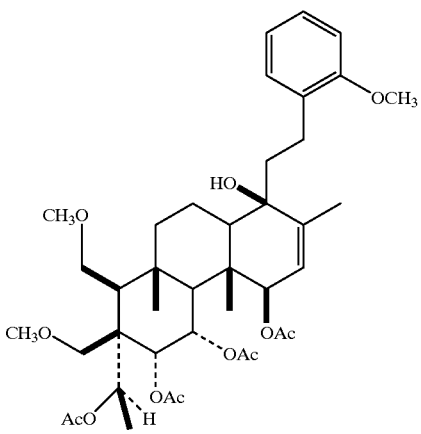

III

Also within the scope of the present invention is a method of treating a condition in a mammal, the treatment of which is effected or facilitated by $K_v1.3$ inhibition, comprising the administration, in an amount that is effective at inhibiting $K_v1.3$, of a compound of Formula I.

An embodiment of this apect of the invention is the method of treating a condition in a mammal the treatment of which is effected or facilitated by $K_v1.3$ inhibition, wherein the condition is selected from the group consisting of: resistance by transplantation of organs or tissue, graft-versus-host diseases brought about by medulla ossium transplantation; rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, bronchial asthma, allergic asthma, intrinsic asthma, extrinsic asthma and dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth; muscular dystrophy; Pyoderma and Sezary's syndrome, Addison's disease, ischemia-reperfusion injury of organs which occurs upon preservation, transplantation or ischemic disease, for example, thrombosis and cardiac infraction, endotoxin-shock, pseudomembranous colitis, colitis caused by drug or radiation, ischemic acute renal insufficiency, chronic renal insufficiency, toxinosis caused by lung-oxygen or drug, for example, paracort and bleomycins, lung cancer, pulmonary emphysema, cataracta, siderosis, retinitis, pigmentosa, senile macular degeneration, vitreal scarring, corneal alkali burn; dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy; disease caused by histamine or leukotriene-$C_4$ release; Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmention of chemotherapeutic effect, preventing or treating activity of cytomegalovirus infection, HCMV infection, and antiinflammatory activity; and treatment of immunodepression or a disorder involving immunodepression, including AIDS, cancer, senile dementia, trauma, chronic bacterial infection, and certain central nervous system disorders.

A preferred embodiment of the invention is the method as recited above wherein the condition is an autoimmune disease.

A more preferred embodiment of the invention is a method of preventing or treating the resistance to transplantation or :transplantation rejection of organs or tissues into a patient in need thereof, which comprises the administration of a compound of Formula 1.

Another embodiment of the invention is a method of suppressing the immune system in a subject in need thereof, which comprises the administration to the subject of an immune suppressing amount of a compound of Formula I.

A subembodiment of the invention is the method recited above with the coadministration of a second immunosuppressive agent.

Another aspect of the invention is a pharmaceutical formulation comprising a pharmaceutically acceptable carrier and a therapeutically effective amount of the compound of Formula I or a pharmaceutically acceptable crystal form or hydrate thereof.

Another embodiment of this aspect of the invention is a pharmaceutical formulation as recited above, comprising in addition, a second immunosuppressive agent comprising azathioprine, brequinar sodium, deoxyspergualin, mizaribine, mycophenolic acid morpholino ester, cyclosporin, FK-506 and rapamycin.

The compounds of the present invention have asymmetric centers and this invention includes all of the optical isomers and mixtures thereof.

In addition compounds with carbon-carbon double bonds may occur in Z- and E- forms with all isomeric forms of the compounds being included in the present invention.

As used herein, the term "alkyl", unless otherwise indicated, includes those alkyl groups of a designated number of carbon atoms of either a straight, branched, or cyclic configuration. Examples of "alkyl" include methyl, ethyl, propyl, isopropyl, butyl, sec-and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethyl pentenyl, and the like, and includes E and Z forms, where applicable. "Halogen", as used herein, means fluoro, chloro, bromo and iodo.

The term "aryl" is defined as a phenyl or naphthyl ring which is optionally substituted with the substituents listed above at any available carbon atoms. The aryl may also be substituted with a fused 5-, 6-, or 7-membered ring containing one or two oxygens and the remaining ring atoms being carbon, the fused 5-, 6-, or 7-ring being selected from the group consisting of: dioxolanyl, dihydrofuranyl, dihydropyranyl, and dioxanyl.

The term "heteroaryl" as utilized herein, unless specifically defined otherwise, is intended to include the following: a 5 or 6-membered ring substituted with one, two or three heteroatoms selected from O, S, N, and is unsubstituted or substituted with one, two or three substituents selected from the group consisting of: Br, Cl, F, I, ($C_1$–$C_6$)-alkoxy, cyano, nitro, hydroxy, CHO, $CO_2H$, $COC_1$–$C_6$-alkyl, $CO_2C_1$–$C_6$-alkyl, $CONR^{13}R^{14}$, $NR^{13}R^{14}$, $NR^{13}COC_1$–$C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, pyrazinyl, pyridazinyl, pyridinyl, pyrimidinyl, and pyrrolyl which are substituted or unsubstituted as defined above.

In the compounds of Formula I, the heteroaryl group may be optionally substituted with the substituents listed above at any available carbon atom or nitrogen atom (if present), but compounds bearing certain substitutents, directly substituted to a nitrogen may be relatively unstable and are not preferred. The heteroaryl may also be fused to a second 5-, 6-, or 7-membered ring containing one or two oxygens such as: dioxolanyl, dihydrofuranyl, dihydropyranyl, and dioxanyl.

Pharmaceutically acceptable salts include both the metallic (inorganic) salts and organic salts; a list of which is given in Remington's Pharmaceutical Sciences, 17th Edition, pg. 1418 (1985). It is well known to one skilled in the art that an appropriate salt form is chosen based on physical and chemical stability, flowability, hydroscopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

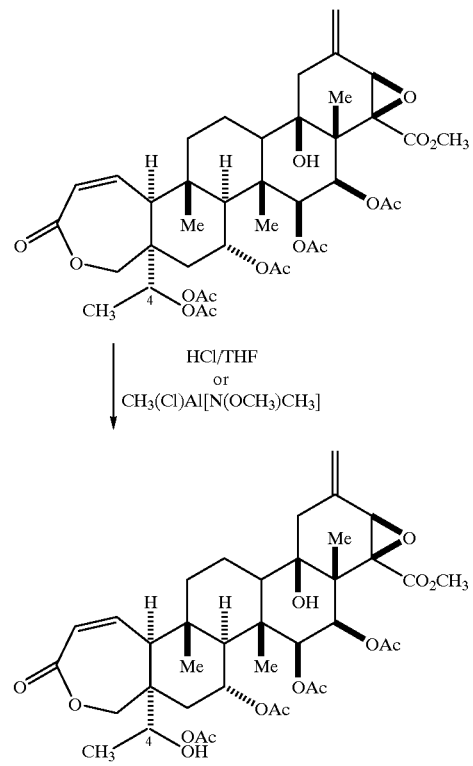

REACTION SCHEME A

As seen in Scheme A, compound I [(4,6,7,15,16-pentakis (acetyloxy)-21,22-epoxy-18-hydroxy-22-methyoxycarbonyl-(6α, 7α, 15β, 16β, 21β, 22β)-D:A-Freido-A-homo-27,30-dinor-24-oxaoleana-1, 20(29)-dien-3-one], isolated from Spachea correa serves as a useful starting material. U.S. Pat. No. 5,631,282 issued on May 20, 1997, describes the isolation of compound I and is hereby incorporated by reference. Lactone I derivatives can be selectively de-acetylated at $C_4$ to give the corresponding alcohol by reacting it with an aqueous solution of HCl (preferably 2M to 3M concentration) in THF. It can also be prepared by reacting I with $CH_3(Cl)Al[N(OCH_3)CH_3$ (Weinreb reagent) in inert solvents such as THF, toluene or methylene chloride.

REACTION SCHEME B

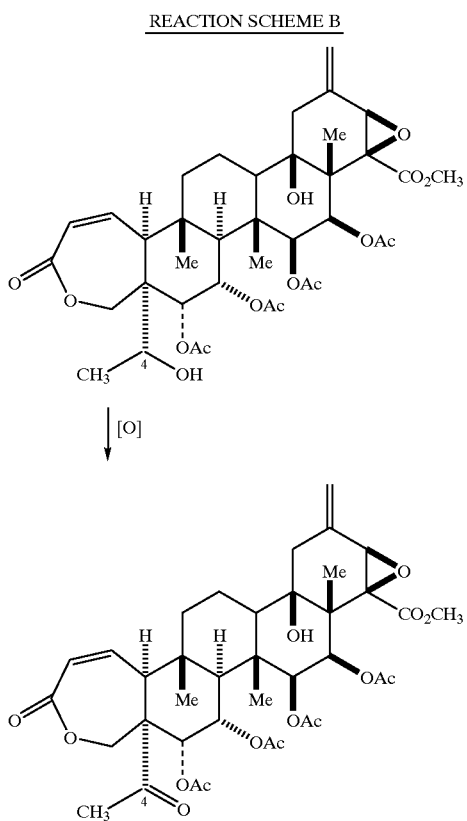

The C4 hydroxy group can be oxidized to the corresponding ketone by a variety of oxidizing agents. The Jones reagent (chromic acid and sulfuric acid in $H_2O$), pyridinium chlorochromate, and oxalyl chloride plus DMSO all will achieve this conversion.

REACTION SCHEME C

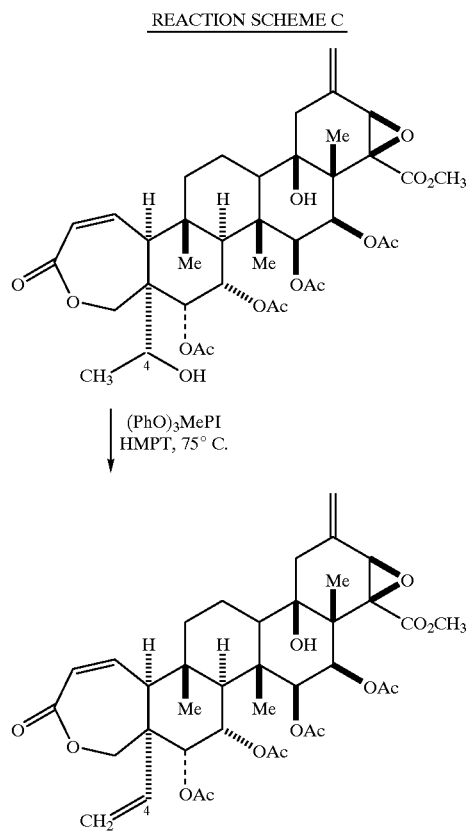

The C4 hydroxy group can also be dehydrated to give the olefin. Reaction of the alcohol with tris-phenoxymethylphosphonium iodide in hexamethyiphosphorous triamide (HMPT) at 75° C. will achieve this conversion.

REACTION SCHEME D

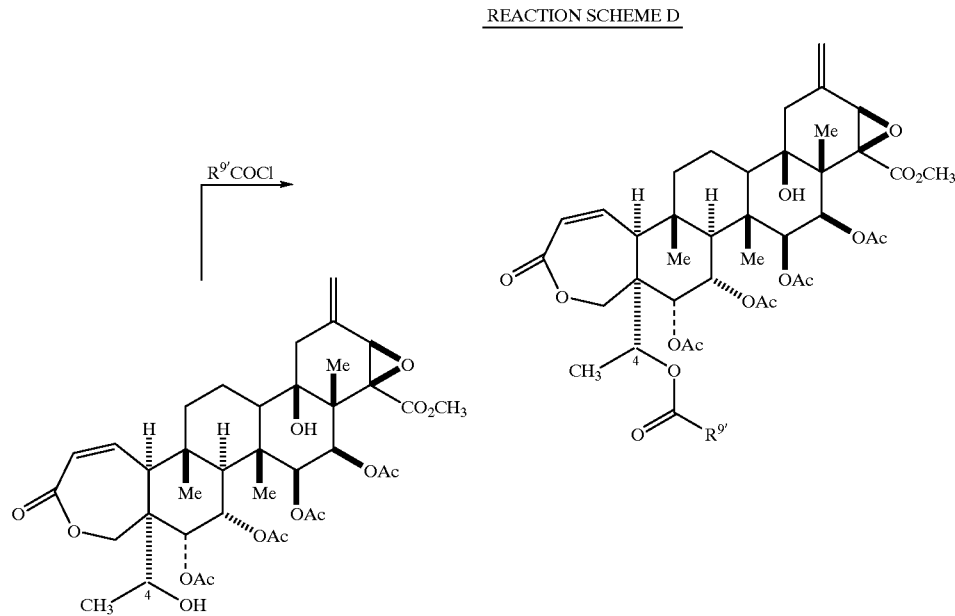

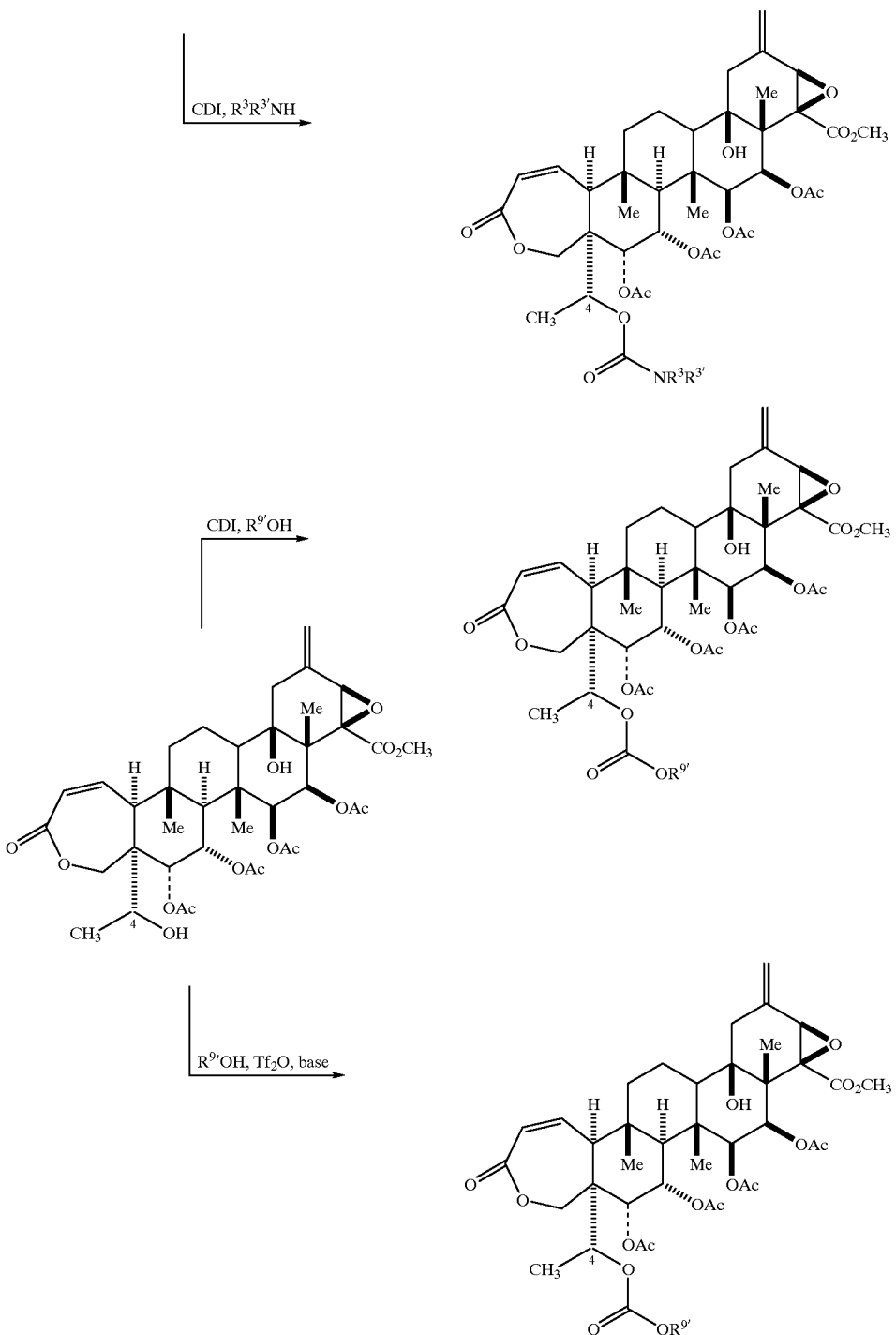

As depicted in Reaction Scheme D, esters at C4 can be prepared by reaction of a preformed carboxylic acid chloride with the C4 alcohol derivative (Reaction Scheme A) in a basic solvent such as pyridine. It should be understood that $R^{9'}$ is used to represent a portion of the $R^9$ definition, e.g. $R^9$ can be an alkyl carbonate which is depicted in the scheme as $OC(=O)OR^{9'}$, $R^{9'}$ representing the alkyl substituent. The acid chlorides, when not purchased, are prepared by stirring the carboxylic acids in reagents such as oxalyl chloride or thionyl chloride. Esters may also be prepared by reaction of the acid chloride and C4 alcohol with silver cyanide (AgCN) in an aprotic solvent such as HMPA. C4 sulfonate derivatives are prepared in a similar manner by reaction with sulfonyl chlorides.

C4 carbonate and carbamate derivatives are prepared by first reacting the C4 alcohol derivative with carbonyldiimidazole (CDI) to obtain the imidazolecarbonyl intermediate which is then reacted with an alcohol or amine ($R^3R^{3'}NH$) to give the corresponding carbonate or carbamate derivatives.

C4 ether derivatives can also be prepared. The best procedure involves reacting an alcohol with trifluoromethanesulfonic anhydride (Tf$_2$O, triflic anhydride) to obtain the preformed triflate in dichloromethane at reduced temperature, preferably −78° C. To this solution is added the triterpene alcohol, the reaction mixture is warmed to room temperature and stirring is continued until reaction is complete. Ethers may also be prepared by heating a mixture of triterpene C4 alcohol, the appropriate alkylhalide and an excess of silver oxide (Ag$_2$O) in an aprotic invert solvent such as THF.

REACTION SCHEME E

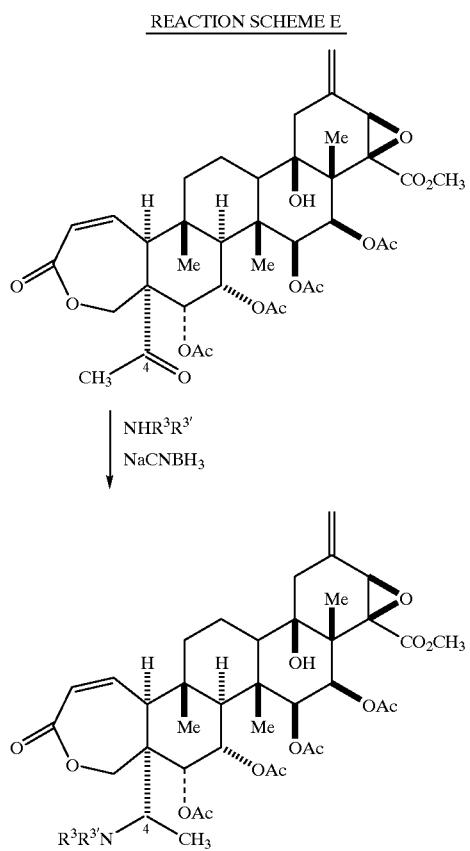

Amines at C4 can be prepared from the C4 ketone described in Reaction Scheme B by reaction with an amine NHR$^3$R$^{3'}$ in a variety of solvents with a reducing agent such as sodium cyanoborohydride.

REACTION SCHEME F

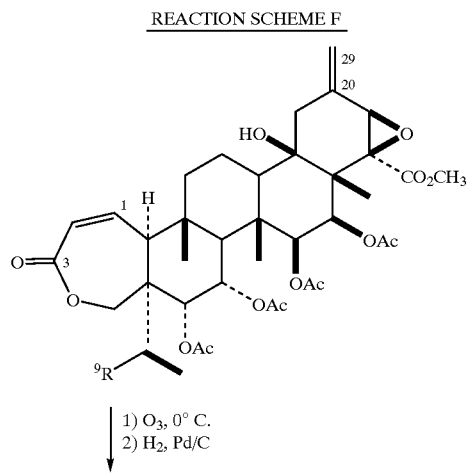

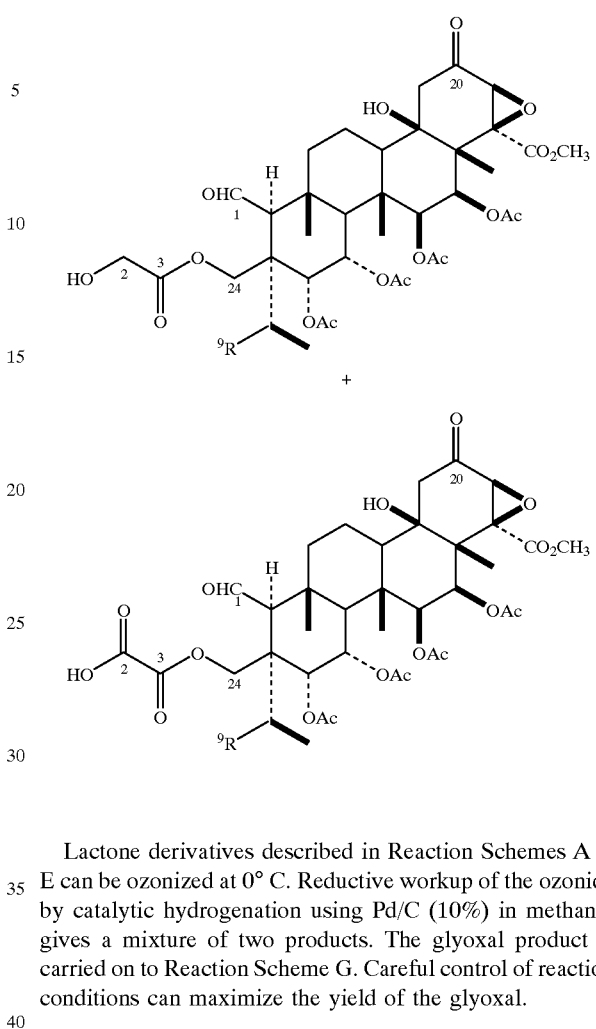

Lactone derivatives described in Reaction Schemes A to E can be ozonized at 0° C. Reductive workup of the ozonide by catalytic hydrogenation using Pd/C (10%) in methanol gives a mixture of two products. The glyoxal product is carried on to Reaction Scheme G. Careful control of reaction conditions can maximize the yield of the glyoxal.

REACTION SCHEME G

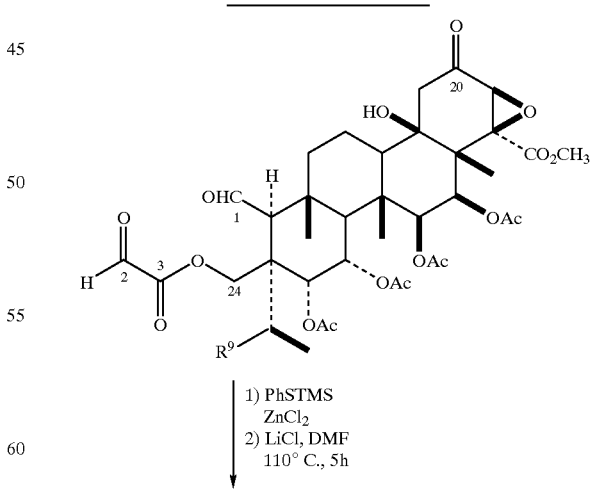

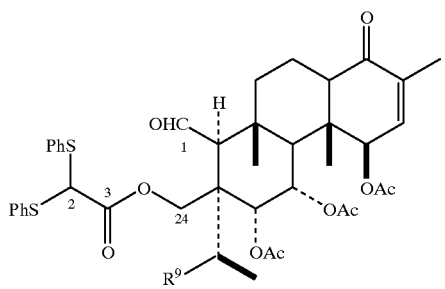

In Reaction Scheme G, the glyoxal is selectively protected as its phenyl thioketal. In this case, trimethylsilylthiophenol catalyzed by $ZnCl_2$ is an effective method. Reaction of this compound with a metalhalide such as LiCl in a solvent such as DMF or DMSO at elevated temperatures such as 100° C. results in ring fragmentation to obtain the depicted tricyclic ketone.

REACTION SCHEME H

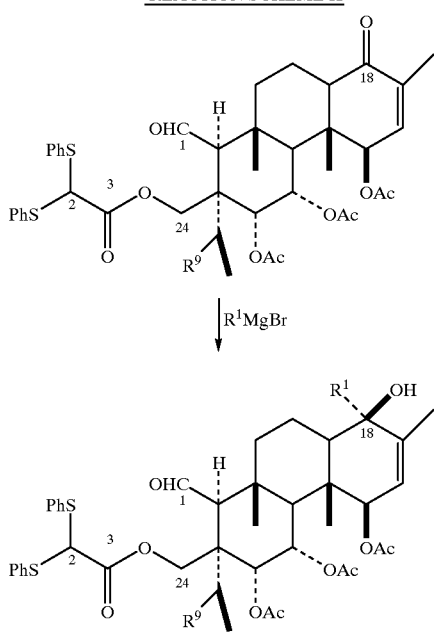

The C18 ketone can be selectively reacted with nucleophiles ($R^{1-}M^+$) to give C18 substituted hydroxy derivatives. Grignard ($R^1MgBr$) or allylsilane reagents are preferred for this transformation. The nucleophile adds from the less hindered alpha face of the molecule, giving predominantly the depicted product.

REACTION SCHEME I

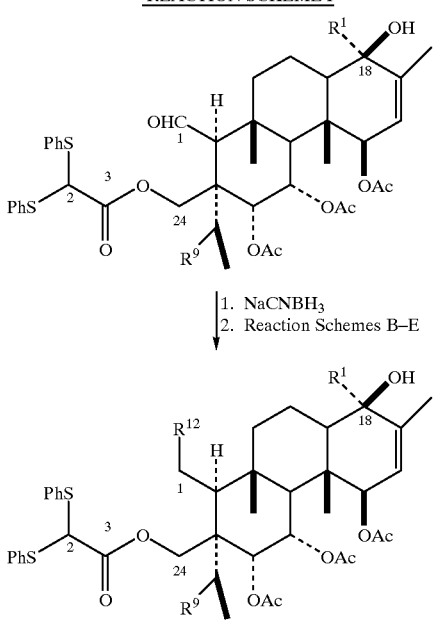

Reaction of the product from Reaction Scheme H with $NaCNBH_3$ selectively reduces the C1 aldehyde to its corresponding alcohol. It can the be transformed as described in reaction schemes B to E. For instance, reaction with methyltriflate provides the methyl ether derivative.

REACTION SCHEME J

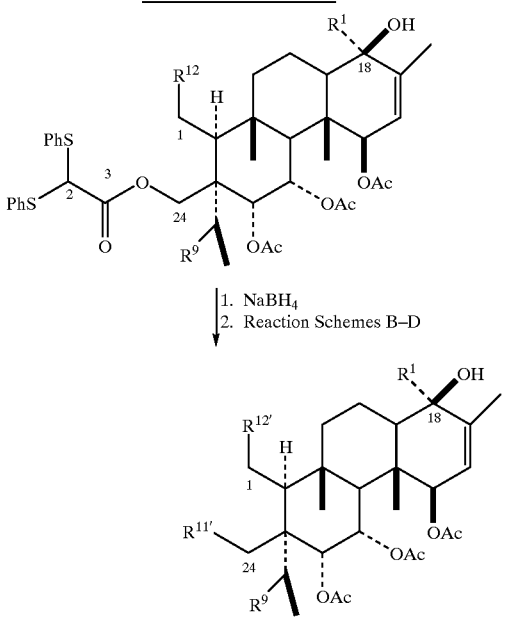

The glyoxal protecting group is removed by reduction with $NaBH_4$ to give the corresponding alcohol, which can be further transformed as described in Reaction Schemes B to E.

REACTION SCHEME K

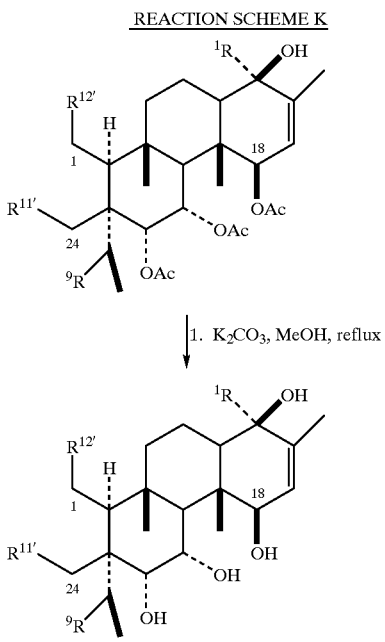

1. K$_2$CO$_3$, MeOH, reflux

The remaining acetate groups can be removed by reaction with K$_2$CO$_3$ in refluxing methanol.

REACTION SCHEME L

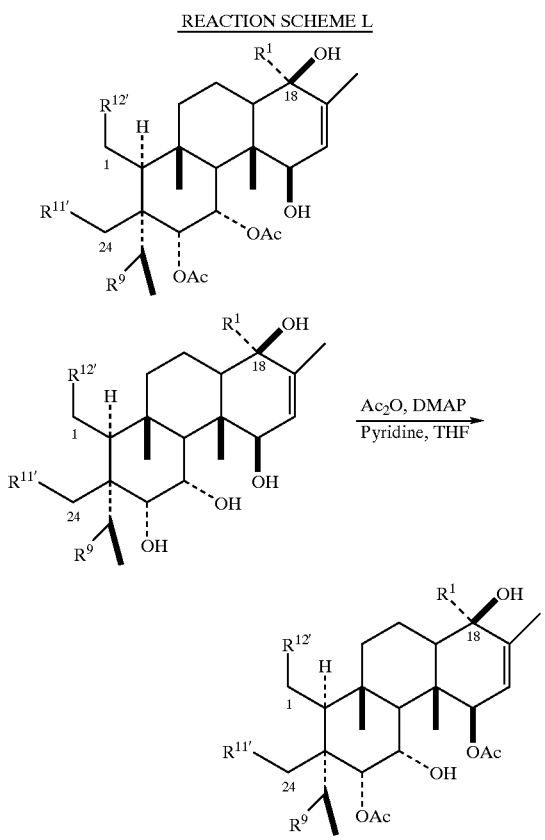

Ac$_2$O, DMAP
Pyridine, THF

Treatment of the hydroxy derivative from Reaction Scheme K with acetic anhydride in pyridine and THF gives a mixture of the C15 and C7 hydroxy derivatives shown in this scheme. Similar reactions can be performed on this material as described in Reaction Scheme D.

REACTION SCHEME M

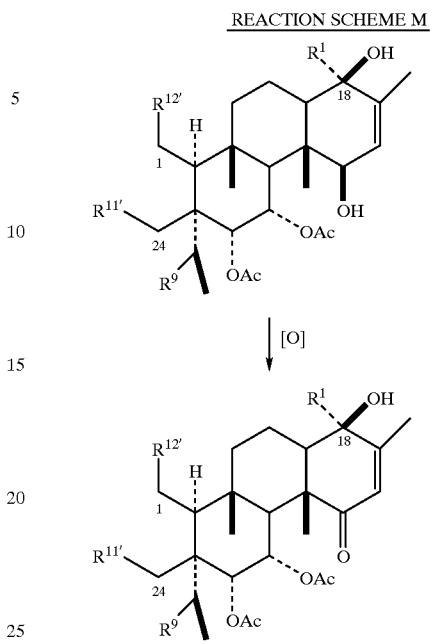

[O]

The C15 hydroxy group can be oxidized to the corresponding ketone by a variety of oxidizing agents. The Jones reagent (chromic acid and sulfuric acid in H$_2$O), pyridinium chlorochromate, and oxalyl chloride plus DMSO all will achieve this conversion.

Tricyclic compounds claimed in this application are also prepared from from readily available racemic and/or optically active starting materials. Reaction Schemes N to Z describe variants of one such route.

REACTION SCHEME N

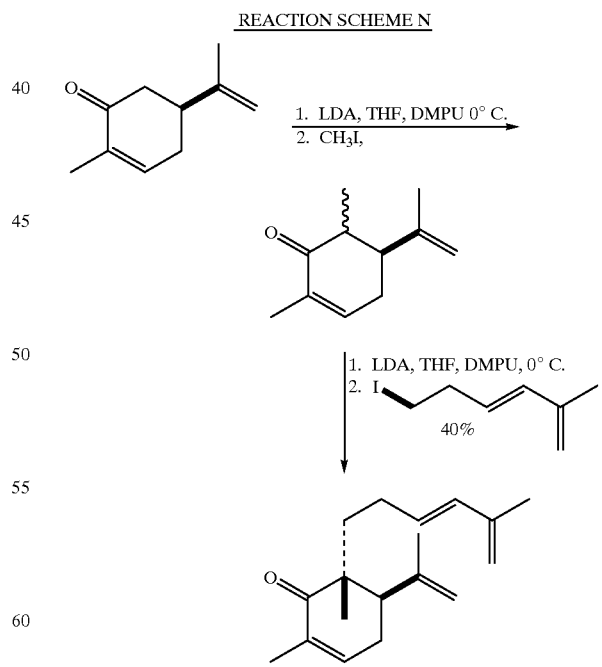

1. LDA, THF, DMPU 0° C.
2. CH$_3$I,

1. LDA, THF, DMPU, 0° C.
2. I

40%

Kinetic deprotonation of S-(+) carvone with LDA in THF and DMPU at 0° C. and subsequent addition of methyl iodide gives 6 methyl carvone as described by Gesson et. al. (Tetrahedron Lett., 27, 4461–4464, 1986). Also as described in the same manuscript, a second kinetic deprotonation with LDA, in the same solvents followed by addition of the depicted iodohexadiene gives exclusively the disubstituted carvone with the indicated configuration.

REACTION SCHEME O

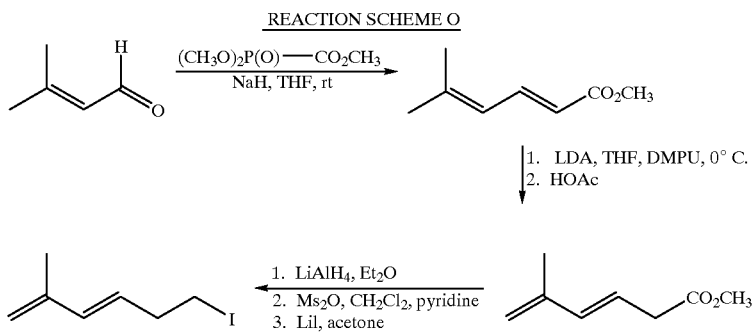

The iodohexadiene reagent is prepared in Reaction Scheme O. The 5-methylhexadienol precursor is prepared as described by Joyce, Gainor and Weinreb (J. Org. Chem., 52, 1177–1185, 1987). It is converted to the methanesulfonate ester, and then to the iodide under standard conditions.

REACTION SCHEME P

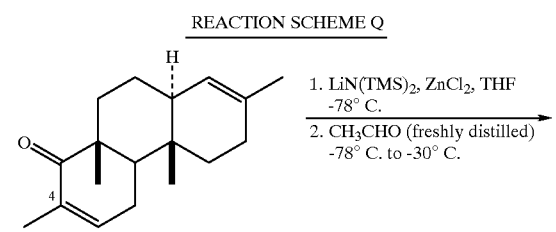

REACTION SCHEME Q

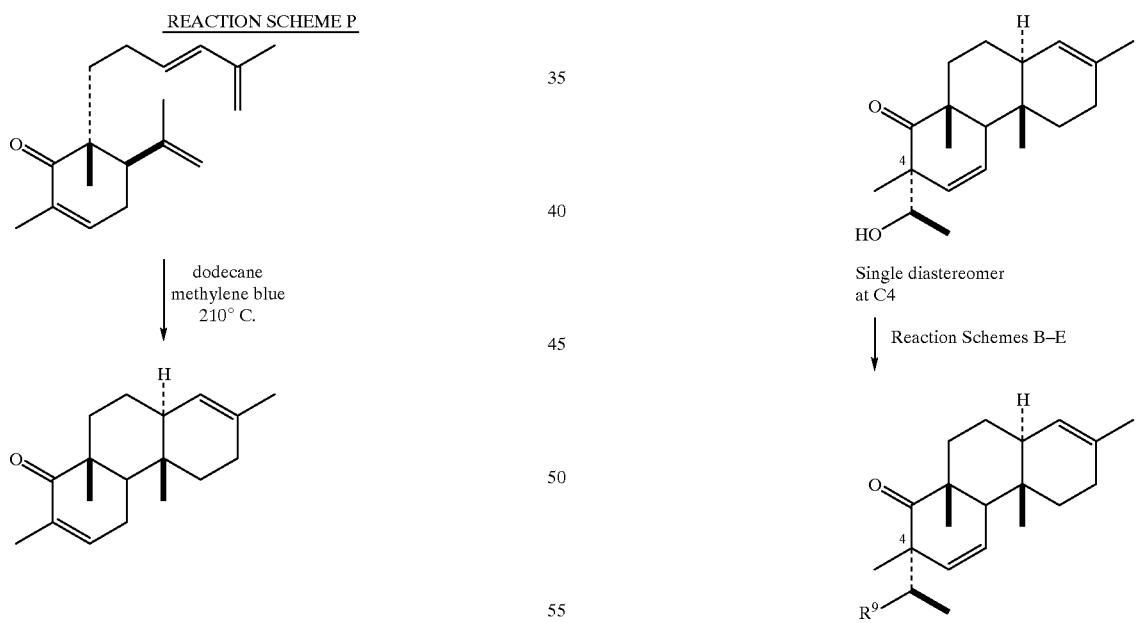

Heating a solution of the diene derivative with a small amount of methylene blue in dodecane at 210° C. effected the Diels Alder reaction giving the energetically favored, trans-anti-trans tricyclic product as the major product. The cyclization of alternately substituted dienes have also been described. Thus, other substitution patterns are permitted. (Gesson et. al. Tetrahedron Lett., 27, 4461–4464, 1986; Abad, et. al., Synlett., 913–915, 1996).

Deprotonation of the tricyclic product from Reaction Scheme P with a base such as LiN(TMS)2 in THF with DMPU (N,N'-dimethylpropyleneurea) followed by addition of $ZnCl_2$ produced the Zinc enolate. Addition of acetaldehyde to the reaction mixture followed by warming to −30° C. affected the chelation-controlled aldol addition producing a single isomer at C4. This hydroxy derivative can be further elaborated as described in Reaction Schemes B to E.

REACTION SCHEME R

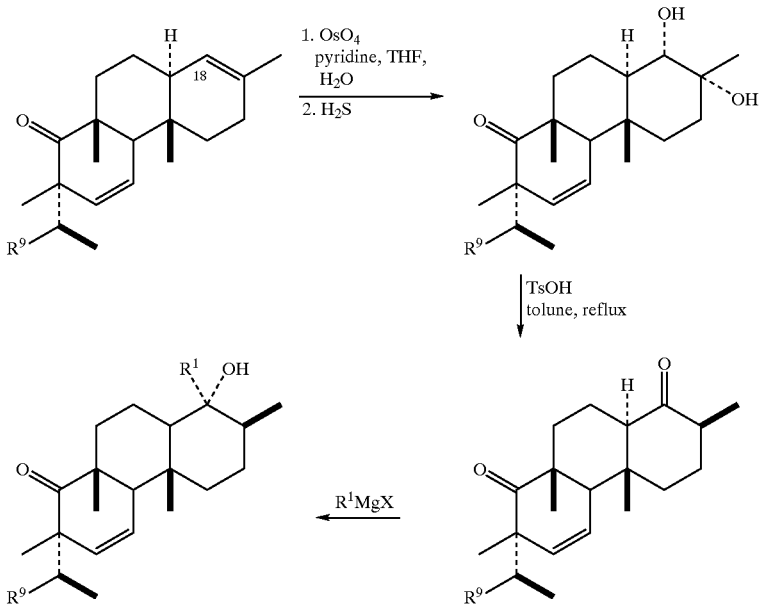

The C17–C18 olefin is efficiently converted to the C18 ketone by a 2-step process. Osmylation under stoichiometric or catalytic conditions with NMO (N-methylmorpholine-N-oxide) gives the diol with the indicated configuration (less hindered face). Heating this compound in refluxing toluene with TsOH (PTSA) affected dehydration to the corresponding ketone as a single diastereomer. The ketone is then elaborated as described in Reaction Scheme H.

tricyclic ketone containing an alcohol, ester or amide substitution at $R^9$ with $LiAlH_4$ in THF at $-78°$ C. gave the depicted triol. Reaction of this with acetone dimethylacetal and a catalytic amount of acid such as PTSA or PPTS (pyridinium p-toluene sulfonate) affected formation of the acetal, now exposing the $C_6$–$C_7$ olefin from the alpha (bottom) face. Osmylation proceeds smoothly giving the

REACTION SCHEME S

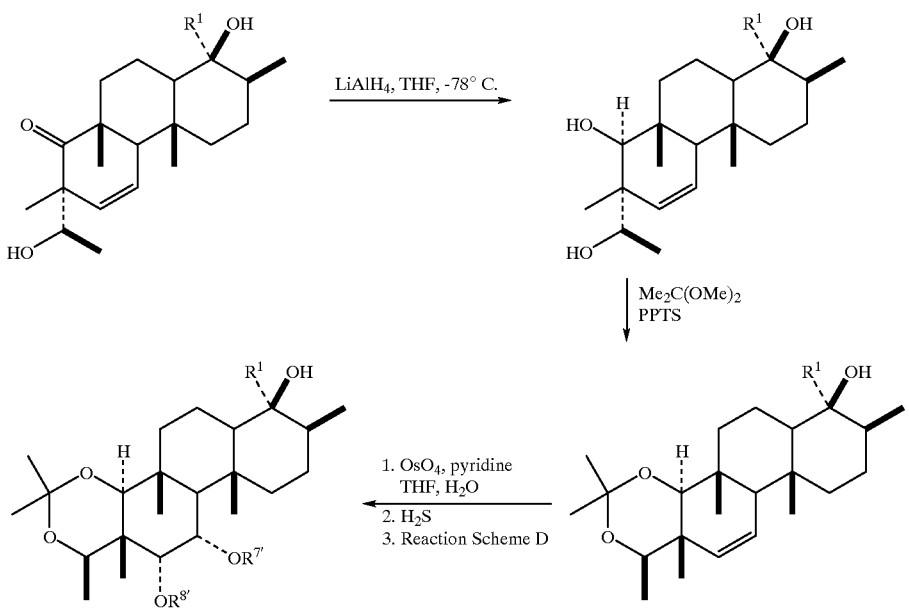

Attempts to osmylate the C6–C7 olefin proved unsuccessful due to the steric interference from the C4 sidechian. This problem was solved in Reaction Scheme S. Reaction of the bis-hydroxy derivative after workup. The two hydroxy groups can be dervatized as described in Reaction Scheme D.

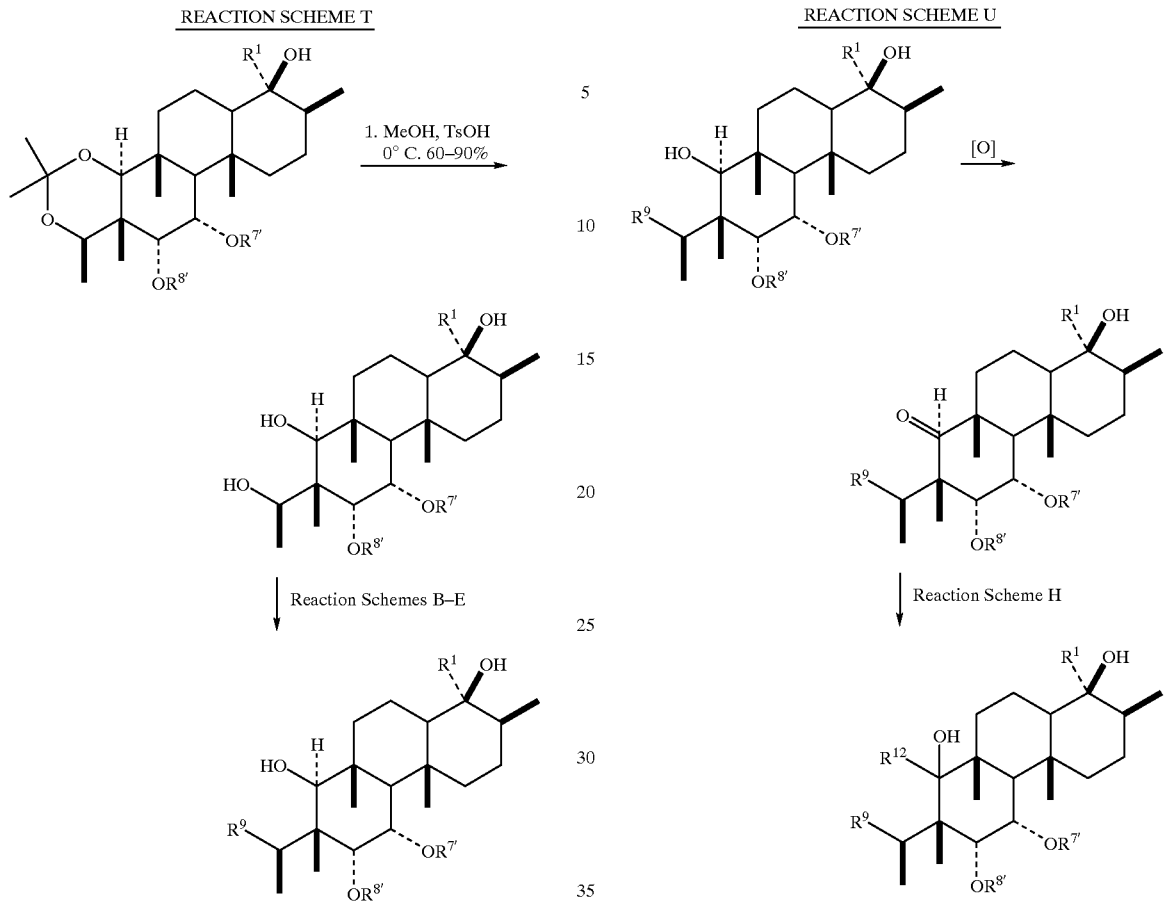

The acetal is removed under mild acidic conditions. Since the C4 hydroxy group is less hindered than the C10 group, it can be selectively derivatized using selected procedures described in Reaction Schemes B to E.

Alternatively, the C10 hydroxy group can be oxidized using PCC (pyridinium chlorochromate) to the corresponding ketone, then further modified by a variety of methods, including, but not limited to procedures described in Reaction Scheme H.

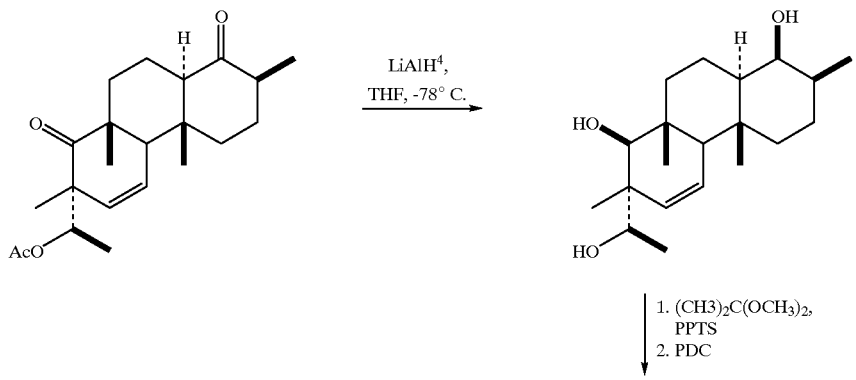

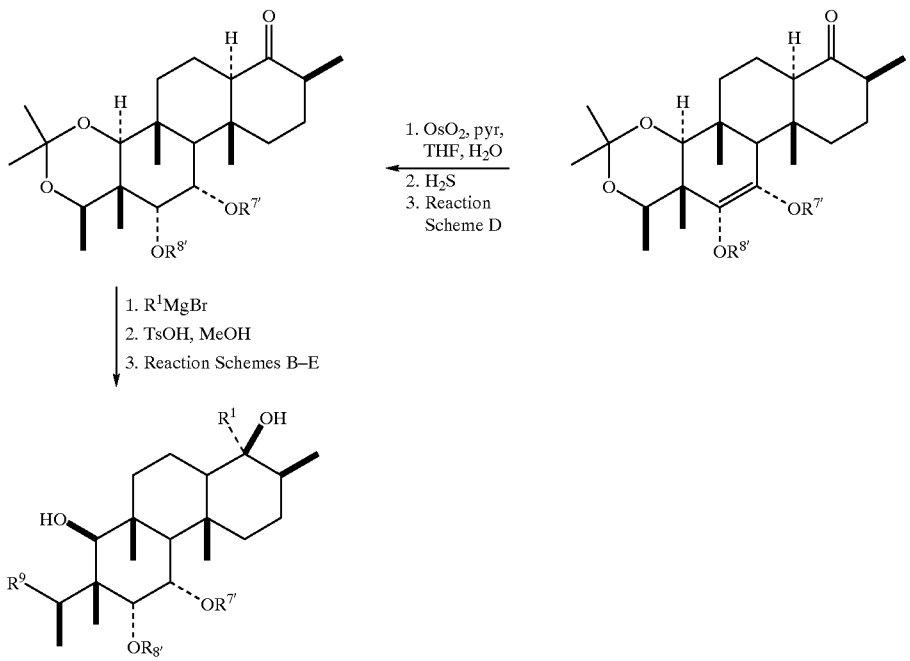

Reaction Scheme V is a variation of Reaction Schemes R, S and T. The diketone (Reaction Scheme R) is first reduced with LiAlH4 in as in Reaction Scheme S to give the triol. Reaction of this with acetone dimethylacetal and a catalytic amount of acid such as PTSA or PPTS (pyridinium p-toluene sulfonate) affected formation of the acetal, now exposing the C6–C7 olefin from the alpha (bottom) face (Reaction Scheme S). The remaining hydroxy group is oxidized to the corresponding ketone via any number of methods. Particularly effective is pyridinium dichromate (PDC). Osmylation proceeds smoothly giving the bis-hydroxy derivative after workup. The two hydroxy groups can be dervatized as described in Reaction Scheme D. The ketone is then elaborated as described in Reaction Scheme H, then modified as described in Reaction Schemes T and U.

UTILITY

The present invention is related to compounds of Formula I, including but not limited to those specified in the examples, which are useful in a mammalian subject for the treatment and prevention of immunemediated diseases such as the resistance by transplantation of organs or tissue such as heart, kidney, liver, medulla ossium, skin, cornea, lung, pancreas, intestinum tenue, limb, muscle, nervous, duodenum, small-bowel, pancreatic-islet-cell, including xeno transplants, etc.; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, and the like; and further infectious diseases caused by pathogenic microorganisms. Further uses may include the treatment and prophylaxis of inflammatory and hyperproliferative skin diseases and cutaneous manifestations of immunologically mediated illnesses, such as psoriasis, atopical dermatitis, contact dermatitis and further eczematous dermatitises and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucous and blood vessels such as gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastrointestinal tract (e.g. migraine, rhinitis and eczema); renal diseases such as interstitial nephritis, Good-pasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fascitis;

periodontal disease such as lesions of gingiva, periodontium, alveolar bone and substantia ossea dentis; nephrotic syndrome such as glomerulonephritis; male pattern alopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g. necrosis caused by toxin, viral hepatitis, shock, or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases such as augmention of chemotherapeutic effect, preventing or treating activity of cytomegalovirus infection, particularly HCMV infection, and antiinflammatory activity.

The compounds of the present invention may also be used in the treatment of immunodepression or a disorder involving immunodepression, such as AIDS, cancer, senile dementia, trauma (including wound healing, surgery and shock) chronic bacterial infection, and certain central nervous system disorders.

Using the methodologies described below, representative compounds of the invention were evaluated and found to be active thereby demonstrating and confirming the utility of the compounds of the invention as $K_v1.3$ inhibitors and immunosuppressants.

T CELL IL-2 ASSAY

Peripheral blood mononuclear (MNC) cells from healthy donors were separated by density centrifugation with ficoll-hypaque (LSM, Organon Teknika, Durham, N.C.), followed by rosetted with neuraminidase treated sheep red blood cells (SRBC). After another centrifugation with leucocyte separation medium (LSM), the SRBC of the rosetted T cells were then lysed with ammonium chloride lysing buffer (GIBCO, Grand Island, N.Y.). Such purified T cells were resuspended at $3 \times 10^6$/mL in RPMI 1640 culture medium (GIBCO) supplemented with 10% fetal calf serum (Sigma, St. Louis, Mo.), 100 mM glutamine, 1 mM sodium pyruvate, 0.1 mM non-essential amino acids, and 1% penn-strep (GIBCO). The cell suspension was immediately distributed into 96 well round-bottom microculture plates (Costar) at 200 $\mu$L/well. The various dilutions of test compound were then added in triplicate wells at 25 $\mu$L/well, incubated for 30 min at 37° C. Ionomycin (125 ng/mL), and PMA (1 or 5 ng/mL), were added to the appropriate wells. The culture plates were then incubated at 37° C. in a humidified atmosphere of 5% $CO_2$—95% air for 18–24 hours. The supernatants were removed, and assayed for IL-2 with an IL-2 capture ELISA, using monoclonal anti-IL-2, and biotinylated goat anti-IL-2 antibodies (unconjugated antibodies purchased from R&D System, Minneapolis, MN). The ELISA was developed with streptavidin conjugated peroxidase (Zymed, San Francisco, Calif.) and substrate for peroxidase (Sigma). Mean OD and units of IL-2 of the replicate wells were calculated from standard curve, created with recombinant IL-2 (Collaborative Biomedical Products, Bedford, Mass.) and the results were expressed as concentration of compound required to inhibit IL-2 production of T cells by 50%.

T CELL PROLIFERATION ASSAY

Peripheral blood mononuclear cells (MNC) from healthy donors were separated by density centrifugation with ficoll-hypaque (LSM, Organon Teknika, Durham, N.C.). After washing the MNC with complete media (RPMI 1640 medium with 5% fetal calf serum, 100 mM glutamine, 1 mM sodium pyruvate, 0.1 mM non-essential amino acid, and 1% penn-strep, obtained from GIBCO, Grand Island, N.Y.), they were then irradiated at 7500 RADS, and resuspended at $4-4.5 \times 10^6$ cells/mL in complete media. Another aliquot of MNC were rosetted with neuraminidase treated SRBC. After another centrifugation with LSM, the sheep red blood cells (SRBC) of these rosetted T cells were then lysed with ammonium chloride lysing buffer (GIBCO, Grand Island, N.Y.). After washing 2× with complete media, these purified T cells were also resuspended at $2-2.5 \times 10^6$ cells/mL in complete media. The various dilutions of the compound were added in triplicates at 50 ul/well of a 96 well flat-bottom microculture plate (Costar, Cambridge, Mass.). T cell suspension was then immediately distributed into the wells at 100 ul/well. After incubating the cells with compound for 30 min. at 37° C. in a humidified atmosphere of 5% $CO_2$—95% air, 20 $\mu\Lambda$/well of anti-CD3 (Ortho Diagnostic, N.J.) at final conc. of 0.3 ng/mL was added, followed by 50 $\mu\Lambda$ of the irradiated MNC. The culture plates were then incubated at 37° C. in a humidified atmosphere of 5% $CO_2$—95% air for 72 hours. The proliferation of T lymphocytes was assessed by measurement of tritiated thymidine incorporation. During the last 18–24 hrs. of culturing, the cells were pulse-labeled with 2 $\mu$Ci/well of tritiated thymidine (NEN, Cambridge, Mass.). The cultures were harvested on glass fiber filters using a multiple sample harvester (MACH-II, Wallac, Gaithersburg, Md.). Radioactivity of filter discs corresponding to individual wells was measured by standard liquid scintillation counting methods (Betaplate Scint Counter, Wallac). Mean counts per minute of replicate wells were calculated and the results were expressed as concentration of compound required to inhibit tritiated thymidine uptake of T cells by 50%.

$K_v1.3$—RUBIDIUM EFFLUX ASSAY

CHO cells transfected with $K_v1.3$ channels at site densities of approximately 40,000 sites/cell are plated into 96 well culture plates and maintained in Iscove's Modified Dulbecco's Medium (IMDM, with L-Glutamine and HEPES, JRH Biosciences). Cells are incubated overnight with $^{86}Rb^+$ (3 μCi/mL, Dupont-NEN) in the glutamine supplemented IMDM. After aspiration of the media, 100 μL of Low K Buffer (in mM, 6.5 KCl, 125 NaCl, 1 $CaCl_2$, 2 $MgCl_2$, 10 HEPES, pH adjusted to 7.2 with NaOH) is added to each well followed by 100 μL test samples in Low K Buffer also containing 0.2% BSA and 2 mM ouabain. Samples are tested at either 1 μg/mL for routine screening or at a variety of concentrations encompassing at least 1/10 to 10 times the putative $IC_{50}$ of test compound to determine potency. After a fixed preincubation time, which is usually 10 min, the samples are aspirated. The $K_v1.3$ channels are opened by depolarization of the cells with High K Buffer (final concentrations, in mM, 63.25 KCl, 68.25 NaCl, 1 $CaCl_2$, 2 $MgCl_2$, 10 HEPES, pH adjusted to 7.2 with NaOH) also containing test compounds. To measure $^{86}Rb^+$ efflux through the channels, aliquots of 100 μL are taken from each well after a given time and added to plates containing 100 μL MicroScint-40 (Packard) for counting by liquid scintillation techniques. MicroScint-40 (100 μL) is then added to each well of the cell plate to determine the remaining $^{86}Rb^+$ activity. The efflux counts are normalized for the total amount of $^{86}Rb^+$ that was in the cells by adding the efflux counts to the cell plate counts. Activity is determined by % inhibition of the efflux window that is established using a saturating concentration of margatoxin (MgTX), a 39 amino acid peptide that is a potent blocker of $K_v1.3$ channels ($IC_{50}$=100 pM).

DOSAGE FORMS

As immunosuppressives, these compounds are useful in the treatment of autoimmune diseases, the prevention of rejection of foreign organ transplants and/or related afflictions, diseases and illnesses.

The compounds of this invention can be administered for the treatment of autoimmune diseases, the prevention of rejection of foreign organ transplants and/or related afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1–500 milligrams per day. Ordinarily, from 10 to 100 milligrams per day in one or more applications is effective to obtain desired results. These dosages are the effective amounts for the treatment of autoimmune diseases, the prevention of rejection of foreign organ transplants and/or related afflictions, diseases and illnesses.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences,* A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention can be illustrated as follows:

CAPSULES

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

SOFT GELATIN CAPSULES

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol. The solution is made to volume with water for injection and sterilized.

SUSPENSION

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The following examples illustrate the preparation of the compounds of Formula I and as such are not to be considered as limiting the invention set forth in the claims appended hereto.

EXAMPLE I

A Method Of Extracting The Compounds Of Formula 1(a) and 1(b) From *Spachea correa*

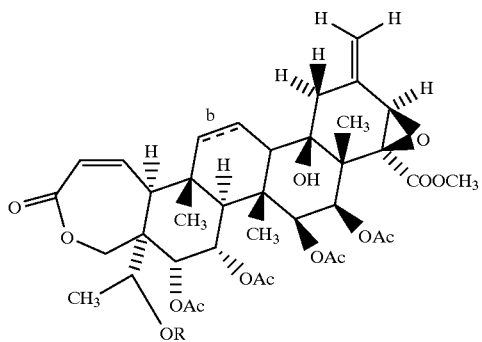

Formula 1(a) b is a single bond and R is OAc
Formula 1(b) b is a double bond and R is OAc One gram of an ethanol extract of the roots of Spachea correa was partitioned between 100 ml of hexane (twice) and 100 ml of 90% aqueous methanol. After separation of the phases, the defatted methanol was concentrated down under vacuum to give an aqueous suspension. This was diluted out to 100 ml with water and extracted, with 100 ml of methylene chloride.

The bioactive methylene chloride extract was dried down to give 12 mg of residue. This was first fractionated by preparative thin layer chromatography (TLC) on a 20 cm by 20 cm E. Merck silica gel $60F_{254}$ plate of 1 mm thickness using methylene chloride-ethyl acetate 1:1 (v/v) as solvent, then by high performance liquid chromatography (HPLC) using a ZORBAX RxC$_8$4.6 mm×25 cm column, operated at 50° C. and eluted with a 50 minute gradient of acetonitrile-:water (1:1, v/v) to 100% acetonitrile, delivered at 1 ml/min, to afford compounds 1(a) and 1 g 1(b).

Homogeneity of the preparations was ascertained in several TLC systems, such as E. Merck silica gel $60F_{254}$, methylene chloride-ethyl acetate 1:1, Rf 1(a) 0.4, Rf 1(b) 0.3; Whatman $KC_{18}$, methanol-water 9:1, Rf 1(a) 0.65, Rf 1(b) 0.75 and by HPLC using a ZORBAX $RxC_8$ column, acetonitrile-water 3:2, k' 1(a) 4.15, k' 1(b) 3.30; and by NMR.

Mass spectra were recorded on JEOL SX-102A (electron impact, EI,903V) and JEOL HX110 (Fast Atom Bombardment, FAB) mass spectrometers. Exact mass measurements were performed at high resolution (HR-EI) using perfluorokerosene (PFK) as the internal standard. Trimethylsilyl derivatives were prepared with a 1:1 mixture of BSTFA-pyridine at room temperature The FAB spectrum was run in a matrix of dithiothreitol (20/80).

The compound of Formula 1(a) runs underivatized by EI. The molecular ion is observed a m/z 788 and three successive loses of acetic acid are observed. The base peak is observed a m/z 334. The compound does not silylate. Scanning HR-EI indicated a molecular formula of $C_{40}H_{52}O_{16}$. A table of the critical HR-EI data is given below.

| Observed m/z | Formula | Assignment |
|---|---|---|
| 788.3220 | $C_{40}H_{52}O_{16}$ | M+ |
| 728.3040 | $C_{38}H_{48}O14$ | M – acetic acid |
| 668.2834 | $C_{36}H_{44}O_{12}$ | M – 2 × acetic acid |
| 334.1417 | $C_{18}H_{22}O_6$ | base peak |

$^{13}$C NMR spectra were recorded for the compound of Formula 1(a) in $CD_2Cl_2$ at 100 MHz on a Varian Unity 400

NMR spectrometer at 20° C. Chemical shifts are given in ppm relative to tetramethylsilane (TMS) at zero ppm using the solvent peak at 53.8 ppm as internal standard. The following data were observed: 15.0, 15.2, 16.8, 17.1, 20.7*, 20.9, 21.1, 21.6, 21.8, 22.2, 35.6, 40.8*, 42.1, 43.6, 45.1, 47.5, 49.3*, 53.5, 59.1, 62.6, 63.5, 66.1, 66.7*, 68.4*, 69.9, 73.9, 75.0, 75.6, 77.1*, 119.4, 123.7, 138.9, 143.0, 167.7, 169.2, 169.3*, 170.25, 170.31, 170.8, 171.3 ppm (where the * signifies the observation as broad resonances). The carbon count of 40 is in agreement with the molecular formula $C_{40}H_{52}O_{16}$ derived by scanning HR EI-MS.

The $^1H$ NMR spectra of compound of Formula(a) was recorded at 400 MHz in $CD_2Cl_2$ on a Varian Unity 400 NMR spectrometer at 25° C. Chemical shifts are in ppm relative to TMS at zero ppm using the solvent peak at 85.32 as the internal standard.

The mass spectra of the compound of Formula 1(b) was obtained as above. The following results were obtained.

| Observed m/z | Formula | Assignment |
|---|---|---|
| 786.3075 | $C_{40}H_{50}O_{16}$ | M+ |
| 726.2886 | $C_{38}H_{46}O14$ | M − acetic acid |
| 666.2651 | $C_{36}H_{42}O_{12}$ | M − 2 × acetic acid |
| 606.2451 | $C_{34}H_{38}O_{10}$ | M − 3 × acetic acid |
| 489.2099 | $C_{26}H_{33}O_9$ | base peak |
| 471.1992 | $C_{26}H_{31}O_8$ | |

$^{13}C$ NMR spectra were recorded for the compound of Formula 1(b) using the procedure described above. The following results were observed: 14.8, 14.9, 17.3, 20.8, 20.9, 21.3, 21.7, 21.8, 21.9, 27.1, 35.1, 40.6, 42.3, 45.4, 48.1, 50.4, 53.5, 54.1, 57.8, 63.7, 66.2, 67.8, 68.6, 71.4, 73.3, 73.8, 74.4, 119.5, 121.1, 124.3, 137.1, 138.9, 143.3, 167.6, 168.6, 169.3, 169.5, 169.9, 171.0, 171.7 ppm.

The carbon count of 40 is in agreement with the molecular formula $C_{40}H_{50}O_{16}$ derived by scanning HR EI-MS.

EXAMPLE II
A Method Of Extracting The Compounds Of Formula 1(c) And 1(d) From *Spachea Correa*

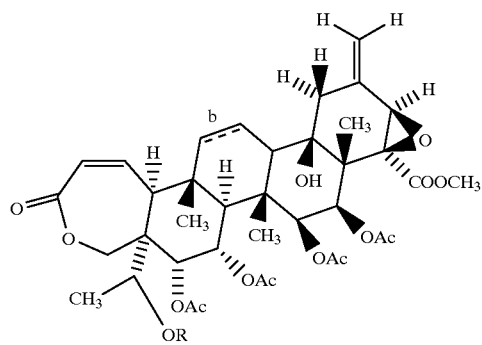

Formula 1(c) b is a single bond and R is OH
Formula 1(d) b is a double bond and R is OH Analogs of the compounds of Formula 1(a) and 1(b) could be detected in the crude extract and fractions thereof when the process of Example 1 was carried out on a larger scale. Thus, 50 g of ethanol extract were partitioned as described in Example 1 using 900 ml of each solvent at each step.

Partial purification of the methylene chloride extract was achieved by column chromatography on E. Merck silica gel 60 (120 ml), eluting with a step gradient of ethyl acetate in methylene chloride. The step gradient was designed so that the column was washed first with 100% methylene chloride and then with methylene chloride-ethyl acetate mixtures of 9:1, 8:2, 3:2, 2:1, 1:1, 1:2, 2:8 and 1:9. Ultimately the column was washed with 100% ethyl acetate. Fractions eluted with methylene chloride-ethyl acetate 3:2 were enriched in compound of Formula 1(a) and 1(b). These were resolved by HPLC using a ZORBAX $RxC_8$ 9 mm×25 cm column, maintained at 50° C. and eluted at 4 ml/min with acetonitrile-water 1:1 v/v. Three identical runs finally afforded 1(a) and 1(b) after crystallization from methanol. Later-eluting fractions from the silica gel column above were found to contain at least two related compounds based on LTV spectra and color reactions on TLC plates. Material from the methylene chloride-ethyl actate 1:1 and 1:2 washings were combined and evaporated down. Separation was achieved on the same HPLC column as above, eluting with a 50 minute gradient of 30% to 50% acetonitrile in water. Two identical runs gave purified compound 1(c). Fractions containing the compound of Formula 1(d) were again processed by HPLC (same column) using acetonitrile-water 3:7 delivered isocratically, to yield the purified compound of Formula 1(d).

The mass spectra of these compounds were recorded on a Finnigan TSQ700 mass spectrometer (electrospray ionization, ESI). The samples were analyzed by LC/MS using a 2.1×50 mm $C_8$ column at 0.2 ml/min. with a mobile phase of 45% acetonitrile/0.01M aqueous ammonium acetate at 50° C. Component 1(d) had a retention time of 10.5 min. and a molecular weight of 744 which is observed a m/z: 745 (M+H), 762 (M+$NH_3$), 786 (M+H+MeCN). Component 1(c) has a retention time of 11.8 min. and a molecular weight of 746 which is observed at m/z: 747 (M+H), 764 (M+$NH_3$) and 788 (M+H+MeCN).

The $^{13}C$ NMR spectra obtained for the compound of Formula 1(c) using the conditions previously described is as follows: 15.1 (2×), 16.9, 19.8, 20.8, 20.91, 20.94, 21.9, 22.3, 35.6, 40.6, 42.2, 43.9, 45.0, 47.7, 50.8, 53.5, 55.6, 61.8, 63.5, 66.0, 67.6 (2×), 69.8, 70.0, 73.9, 75.0, 75.6, 119.3, 123.7, 139.0, 144.4, 167.8, 169.2, 169.5, 170.1, 170.4, 171.4 ppm.

The carbon count of 38 is in agreement with the molecular formula $C_{38}H_{50}O_{16}$ derived by scanning HR EI-MS.

EXAMPLE III
Separation By HPLC
Compounds of this invention were characterized by the following behavior during HPLC separation on a ZORBAX $RxC_8$ 4.6 mm×25 cm column, maintained at 50° C. and eluted at 1 ml/min with acetonitrile-water 3:2 v/v):
Compound 1(a): k'=4.15; 1(b): k'=3.30; 1(c): k'=2.30; 1(d): k'=2.10.

Analyses using this HPLC system can be used to quantify the compounds in the crude extract or other mixtures, by comparing the absorbance of HPLC peaks at a wavelength of 220 nm with that produced by injections of known (weighed) amounts of pure standards.

EXAMPLE IV
Additional Purification Procedure
A simplified purification process allows for rapid fractionation of even larger amounts of crude extract and the preparation of gram amounts of the compounds of Formula 1(a) and 1(b).

The ethanol extract is first dissolved at 20 grams per 150 ml in methanol. This solution is diluted with 150 ml of water and then extracted three times with methylene chloride using 150 ml of methylene chloride each time. The pooled methylene chloride extracts are evaporated down and fractionation proceeds by repeated column chromatography on silica gel. One employs methylene chloride-methanol 97:3 in a first step; the mixed compounds of Formula 1(a) and 1(b) thus obtained are resolved by chromatographing on fresh silica gel eluted with methylene chloride-ethyl acetate 3:1. Volume of elution for the compound of Formula 1(a) ranges from about 2 to about 3.5 column volumes of solvent; that for the compound of Formula 1(b) is about 3 to about 4.5 column volumes. Finally, advantage is taken of the low solubility of these compounds, and, after total resolution by chromatography, the compounds of Formula 1(a) and 1(b) can be precipitated and or crystallized from concentrated methanol solutions.

EXAMPLE 1

1β-S-2α,2β,3α,4α,3aα,4bβ,5β,8aα,10aβ]-2α-(1-R-acetoxyethyl)-2β-(2,2-diphenylthioacetoxymethyl)-1-formyl-8-oxo-2b,4b,7, 10a-tetramethyl-3,4,5-triacetoxy-1,2,3,4,4a,4b,5,8,8a,9,10,10a-dodecahydro-2-[H]-phenanthrene

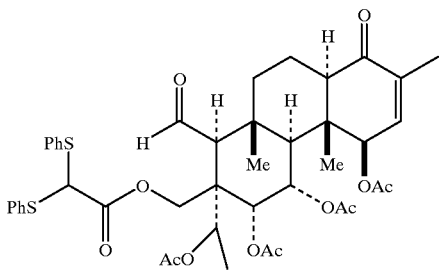

Step 1: [1α-R-1aα,2β,3aβ,3β,5aβ,6β,7β,7β,8α,9α,9aα, 9bβ,10β,11β,11aβ,11bα,11bβ]-7-(1-R-acetoxyethyl)-3a-hydroxy-6-formyl-7-(2-oxoacetoxymethyl)-11b-methoxycarbonyl-2-oxo-8,9,10,11-tetraacetoxy-5a,9b, 11a-trimethyl-1a,2,3,3a,3b,4,5,5a,6,7,8,9,9a,9b,10,11,11a, 11b-octadecahydrocryseno[1,2-b]oxirane

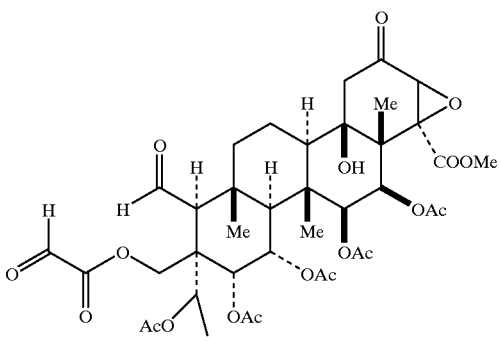

A solution of 10.0 g of 4,6,7,15,16-pentakis(acetyloxy)-21,22-epoxy-18-hydroxy-22-methoxycarbonyl-D:A-Friedo-A-homo-27,30-dinor- 24-oxaoleana-1,20(29)-dien-3-one (see Examples I–IV above) in 150 mL of 1:1 $CH_2Cl_2$-methanol was cooled to 0° C. and a stream of ozone was passed though it. After 120 min the solution was purged with nitrogen for 15 min and placed in a hydrogenation flask. Then 1 g of 10% Pd/C was added and the solution was shaken under 20 psi of hydrogen for 18 h. The solution was filtered though Celite and concentrated to afford the title compound, which was used directly in the next step; $^1H$ NMR ($CDCl_3$)δ 9.65 (d, 1H, J=4.5 Hz); Mass Spectrum (APCI): m/e 840 (M+$NH_4$).

Step 2: [1α-R-1aα,2β,3aβ,3β,5aβ, 6β,7α,7β,8α,9α,9aα, 9bβ,10β,11β,11aβ,11bα,11bβ]-7-(1-R-acetoxyethyl)-3a-hydroxy-6-formyl-7-(2,2-diphenylthioacetoxymethyl)-11b-methoxycarbonyl-2-oxo-8,9,10,11-tetraacetoxy-5a, 9b, 11a-trimethyl-1a,2,3,3a,3b,4,5,5a,6,7,8,9,9a,9b,10,11,11a,11b-octadecahydrocryseno[1,2-b]oxirane

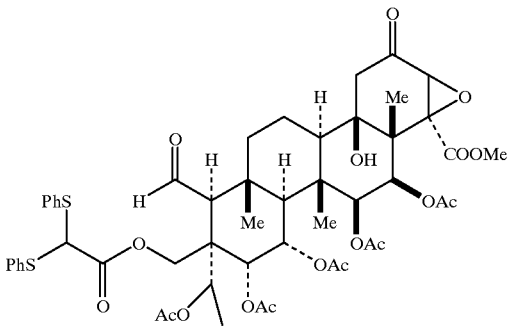

A solution of 7.0 g (8.5 mmol) of 1α-R-1aα,2α,3aβ,3β, 5aβ,6β,7α,7β,8α,9α,9aα,9bβ,10β,11β,11aβ,11bα,11bβ]-7-(1-R-acetoxyethyl)-3a-hydroxy-6-formyl-7-(2-oxoacetoxymethyl)-11b-methoxycarbonyl-2-oxo-8,9,10,11-tetraacetoxy-5a,9b,11a-trimethyl-1a, 2,3,3a,3b,4,5,5a,6,7,8, 9,9a,9b,10,11,11a,11b-octadecahydrocryseno[1,2-b]oxirane, 2.81 g (25.5 mmol) of thiophenole, and 12.06 g (85 mmol) of $BF_3 \cdot OEt_2$ in 25 mL of dry $CH_2Cl_2$ was stirred at 45° C. under nitrogen. After 1 h, the solution was diluted with $CH_2Cl_2$ and the organic mixture was washed with thee portions of saturated aqueous $NaHCO_3$ solution, and then water. The organic extract was dried over $MgSO_4$, filtered and concentrated. The oily residue was filtered through 600 g of silica gel using 2:1 ethyl acetate-hexane to afford the title compound, which was used directly in the next step.

Step 3: [1β-S-2α,2β,3α,4α,3aα,4bβ,5β,8aα,10aβ]-2α-(1-R-acetoxyethyl)-2β-(2,2-diphenylthioacetoxymethyl)-1-formyl-8-oxo-2b,4b,7,10a-tetramethyl-3,4,5-triacetoxy-1,2, 3,4,4a,4b,5,8,8a,9,10,10a-dodecahydro-2-[H]-phenanthrene A solution of 8.8 g (10.2 mmol) of the material from Step B and 1.4 g (33 mmol) of LiCl in dry DMF was heated at 110° C. under nitrogen. After 5 h, the reaction was allowed to cool and the solution was partitioned between ethyl acetate and water. The organic layer was washed with saturated $NaHCO_3$ solution and brine, then was dried over $MgSO_4$, filtered and concentrated. The residue was filtered though silica gel using 1:2 ethyl acetate-hexane and the filtrate was concentrated to an oil. The oily residue was purified by HPLC (Waters RCM silica gel) using a solvent mixture of 3:2 hexane-(5:4:1 hexane-methyl t-butyl ether-hexane) to afford the title compound; $^1H$ NMR ($CDCl_3$)δ 1.78 (s, 3H), 9.72 (d, 1H, J=4 Hz); $^{13}C$ NMR ($CDCl_3$)δ 198.3, 202.7; Mass Spectrum (APCI) mn/e 840 (M+$NH_4$).

EXAMPLE 2

[1β-S-2α,2β,3α,4α,3aα,4bβ,5β,8aα,10aβ-2α-(1-R-acetoxyethyl)-2β-(2,2-diphenylthioacetoxymethyl)-1-formyl-8-(2-(2-methoxyphenyl)ethyl)-8-hydroxy-2b,4b,7,10a-tetramethyl-3,4,5-triacetoxy-1,2,3,4,4a,4b,5,8,8a,9,10,10a-dodecahydro-2-[H]-phenanthrene

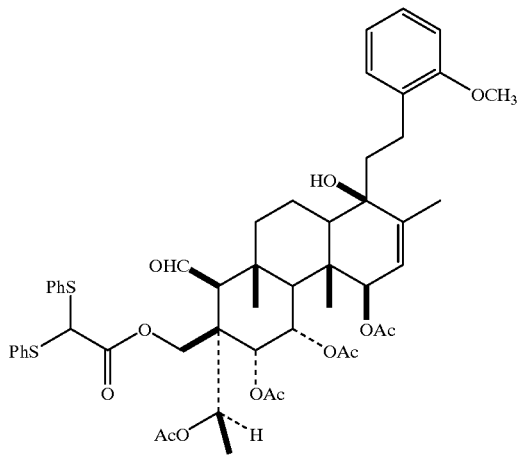

A Grignard reagent was prepared as follows: to a mixture of 42 mg of Mg and 428 mg of 1-bromo-2-(2-methoxyphenyl)ethane in 2 mL of dry ether was added 2 grains of iodine and the mixture was heated at 50° C. The solution was allowed to cool to room temperature after most of the metal had dissolved.

A solution of 100 mg (0.12 mmol) of [1β-S-2α,2β,3α, 4α,3aα, 4bβ,5β,8aα,10aβ]-2α-(1-R-acetoxyethyl)-2β-(2,2-diphenyl thioacetoxymethyl)-1-formyl-8-oxo-2b,4b,7,10a-tetramethyl-3,4,5-triacetoxy-1,2,3,4,4a,4b,5,8,8a,9,10,10a-dodecahydro-2-[H]-phenanthrene in dry THF was cooled to −5° C. and to this was added 0.5 mL of the Grignard reagent described above. The solution was stirred at −5° C. for 1 h, then an additional 0.5 mL of Grignard reagent was added. After 30 min at 0° C., the reaction was quenched by addition of aqueous NH₄Cl and ether and the layers were separated. The organic extracts were washed with brine, dried over MgSO₄, filtered and concentrated. The residue was purified by HPLC (Waters RCM silica gel) using a solvent mixture of 1:1 hexane-(5:4:1 hexane-methyl t-butyl ether-hexane) to afford the title compound; $^1$H NMR (CDCl₃)δ 3.82 (s, 3H), 9.72 (d, 1H, J=4 Hz); $^{13}$C NMR (CDCl₃)δ 202.7; Mass Spectrum (APCI) m/e 966 (M+NH₄).

EXAMPLE 3

1β-S-2α,2β,3α,4α,3aα,4bβ,5β,8aα,10aβ]-2α-(1-R-acetoxyethyl)-1β,2β-bis(hydroxymethyl)-8-(2-(2-methoxyphenyl)ethyl)-8-hydroxy-2b,4b,7,10a-tetramethyl-3,4,5-triacetoxy-1,2,3,4,4a,4b,5,8,8a,9,10,10a-dodecahydro-2-[H]-phenanthrene

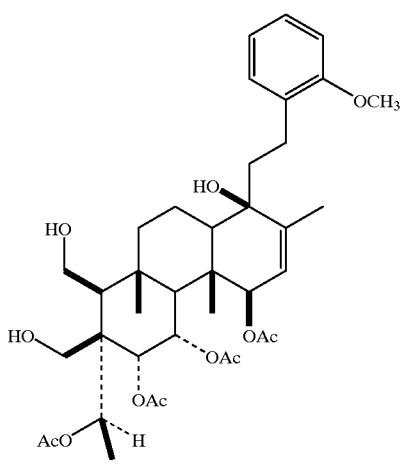

A solution of 0.0.037 g (0.039 mmol) of 1β-S-2α,2β,3α, 4α,3aα,4bβ,5β, 8aα,10aβ]-2α-(1-R-acetoxyethyl)-2β-(2,2-diphenylthioacetoxymethyl)-1-formyl-8-(2-(2-methoxyphenyl)ethyl)-8-hydroxy-2b,4b,7,10a-tetramethyl-3,4,5-triacetoxy-1,2,3,4,4a,4b,5,8,8a, -9,10,10a-dodecahydro-2-[H]-phenanthrene in dry THF was cooled to 0° C. Then 30 mg of solid NaBH₄ was added and the solution was stirred at room temperature. After 20 min, a second 30 mg portion of solid NaBH₄ was added and the solution stirred at room temperature for 15 min. The reaction was quenched by addition of 2 mL of water and the mixture was partitioned between water and dichloromethane. The organic layers were dried over MgSO₄, filtered and concentrated. The oily residue was purified by HPLC (Waters RCM silica gel) using a solvent mixture of 3:2 hexane-(5:4:1 hexane-methyl t-butyl ether-hexane) to afford the title compound; $^1$H NMR (CDCl₃)δ 3.53 (AB, 1H, J=12.5 Hz), 4.06 (AB, 1H, J=12.5 Hz)4.14 (m, J=2H); $^{13}$C NMR (CDCl₃)δ 198.3; Mass Spectrum (APCI) m/e 720 (M+NH₄).

EXAMPLE 4

1β-S-2α,2β,3α,4α,3aα, 4bβ,5β,8aα,10aβ]-2α-(1-R-acetoxyethyl)-1β,2β-bis(methoxymethyl)-8-(2-(2-methoxyphenyl)ethyl)-8-hydroxy-2b,4b,7,10a-tetramethyl-3,4,5-triacetoxy-1,2,3,4,4a,4b,5,8,8a,9,10,10a-dodecahydro-2-[H]-phenanthrene

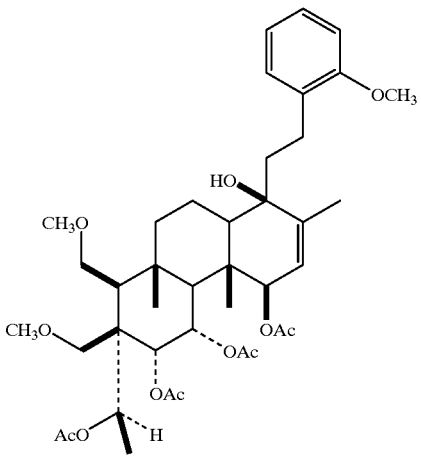

A solution of 0.02 g (0.028 mmol) of 1β-S-2α,2β,3α,4α, 3aα, 4bβ,5β,8aα,10aβ]-2α-(1-R-acetoxyethyl)-1β,2β-bis(hydroxymethyl)-8-(2-(2-methoxyphenyl)ethyl)-8-hydroxy-2b,4b,7,10a-tetramethyl-3,4,5-triacetoxy-1,2,3,4,4a,4b,5,8,8a,9,10,10a-dodecahydro-2-[H]-phenanthrene in 2 mL of dry dichloromethane was stirred at rt under nitrogen. Then 0.19 mL (0.84 mmol) of 2,6-di-t-butylpyridine was added followed by 0.05 mL (0.427 mmol) of methyl triflate. The solution was stirred at 40° C. for 1 h, then additional portions of 0.19 mL (0.84 mmol) of 2,6-di-t-butylpyridine and 0.05 mL (0.427 mmol) of methyl triflate were added. After 1 h, the reaction was quenched by addition of 2 mL of 1N HCl solution and the mixture was partitioned between water and dichloromethane. The organic layers were dried over MgSO$_4$, filtered and concentrated. The oily residue was purified by HPLC (Waters RCM silica gel) using a solvent mixture of 3:2 hexane-(5:4:1 hexane-methyl t-butyl ether-hexane) to afford the title compound; $^1$H NMR (CDCl$_3$)δ 3.26 (s, 3H), 3.27 (s, 3H); Mass Spectrum (APCI) m/e 748 (M+NH$_4$).

EXAMPLE 5

4b-S-4aα,4bβ,8aα,10aβ]-2β-(1-R-acetoxyethyl)-2β-methyl-8-hydroxy-1-oxo-2,4b,7,10a-tetramethyl-1,2,4a,4b,5,6,8a,9,10,10a-decahydro-1-[H]-phenanthrene

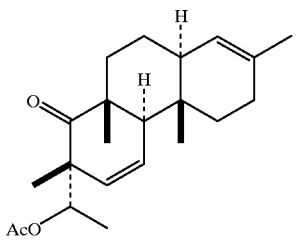

Step 1: Preparation of Methyl 5-methyl-2,4-hexadienoate

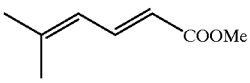

Using a 2 L flask equipped with a mechanical stirrer, a dropping funnel and a mineral oil bubbler, 100 g of trimethyl phosphonoacetate (0.53 mole) were added dropwise to a suspension of 23 g of NaH (60% dispersion in mineral oil; 0.58 mole) in 1500 mL of dry THF at 0° C. to give a thick white paste. Stirring was continued until the evolution of hydrogen ceased (~30 min). Then, 45 g of 3-methyl-2-butenal (52 mL; 0.53 mole) were slowly added and the mixture was gradually warmed to room temperature. After 4 h, the mixture was concentrated and 1000 mL of ether and 200 mL of 2N H$_2$SO$_4$ were added. The organic layer was separated, washed with saturated aq. NaHCO$_3$ and brine, dried over MgSO$_4$ and Filtered. The solvent was removed in vacuo and the oily residue was distilled (65–68° C., 5 Torr or 104° C., 30 Torr) to afford the title compound; $^1$H NMR (CDCl$_3$)δ 1.83 (s, 3H), 1.85 (s, 3H), 3.80 (s, 3H), 5.76 (d, 1H, J=16 Hz), 6.00 (d, 1H, J=16 Hz), 7.58 (m, 1H).

Step 2: Preparation of Methyl 5-methyl-3,5-hexadienoate

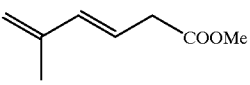

R. P. Joyce, J. A. Gainor, S. M. Weinreb, J. Org. Chem. 1987, 52, 1177.

To a solution of 75 mL of diisopropylamine (0.54 mole) in 1500 mL of dry THF at 0° C. was added 50 mL of n-butyllithium in hexane (10M, 0.5 mole). After stirring the mixture for 15 min, 60 mL of DMPU (63.5 g, 0.5 mole) were added dropwise over 5 min After an additional 30 min, a solution of 63 g of methyl-5-methyl-2,4-hexadienoate (0.45 mole) in 250 mL of THF was added over 45 min, and the mixture was stirred for 3 h at 0° C. The dark red solution was poured into a rapidly stirred solution of 500 mL of 10% acetic acid. The mixture was extracted with hexanes, and the organic extracts were combined, washed with sat. aqueous NaHCO$_3$ and brine, dried over MgSO$_4$ and filtered. The solvent was removed in vacuo and the oily residue was applied to a plug of 150 g of silica gel. The silica gel was washed with hexane, then with 3% ethyl acetate-hexane to afford the title compound. After evaporation, the ester was distilled (68–70° C., 5 Torr or 78° C., 18 Torr); $^1$H NMR (CDCl$_3$)δ 1.87 (s, 3H), 3.17 (d, 2H, J=8 Hz), 3.71 (s, 3H), 4.97 (d, 2H, J=10 Hz), 5.75 (m, 1H), 6.25 (d, 1H, J=16 Hz).

Step 3: Preparation of 5-Methyl-3,5-hexadienol

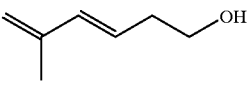

A solution of 5-Methyl-3,5-hexadienoate (30 g, 0.21 mole) in 100 mL of ether was added dropwise to a suspension of LiAlH$_4$ (8.9 g, 0.23 mole) in 250 mL of ether at a rate that maintained a gentle reflux. After 1 h, the excess hydride was destroyed by the careful addition of 6 mL of water, followed by the addition of 12 mL of 15% aquous NaOH and 6 mL of water. The resulting slurry was stirred for 15 min and was filtered. The aluminum salts were thoroughly washed with ether, and the combined filtrates were dried over MgSO₄, filtered and the solvent was removed in vacuo to give the title compound as an oil which was used without further purification; ¹H NMR (CDCl₃)δ 1.85 (s, 3H), 2.38 (m, 2H), 3.70 (m, 2H), 4.93 (s, 2H), 5.64 (m, 1H), 6.27 (d, 1H, J=12 Hz).

Step 4: Preparation of 1-Iodo-5-Methyl-3.5-hexadiene

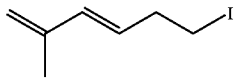

To a solution of 5-Methyl-3,5-hexadienol (6 g, 0.053 mole) in 75 mL of methylene chloride and 12.9 mL of pyridine (12.6 g, 0.16 mole) at 0° C. was added 18.6 g of methanesulfonic anhydride (0.106 mole) in several small portions. After 2 h, the mixture was poured into 250 mL of hexanes. The organic fractions were washed with sat. aqueous NaHCO₃ and brine, dried over MgSO₄, filtered and concentrated to give 11 g of the crude mesylate as an oil.

To a solution of the mesylate in 150 mL of acetone at 0° C. was added 30 g of LiI in several small portions. The mixture was warmed to rt and shielded from light. After 4 h, TLC showed complete disappearance of the mesylate. The mixture was concentrated, poured into 200 mL of H₂O and extracted with hexanes. The combined organic extracts were washed with aquous Na₂S₂O₃ and brine, dried over MgSO₄, and filtered though a plug of silica gel (100 g) eluting with an additional 1000 mL of hexanes. The solvent was removed afford the title compound; ¹H NMR (CDCl₃)δ 1.86 (s, 3H), 2.67 (m, 2H), 3.20 (m, 2H), 4.97 (d, 2H, J =8 Hz), 5.60 (m, 1H), 6.23 (d, 1H, J=16 Hz).

Step 5: Preparation of (S)-6-α,β-Methyl-Carvone

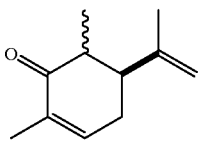

To a solution of 112 mL of diisopropylamine (80.8 g, 0.79 mole) in 1000 mL of dry THF at 0° C. was added 79 mL of n-butyllithium (10M, 0.79 mole) in hexane. After the mixture was stirred for 30 min, (S)-carvone (100 g, 0.66 mole) was added dropwise. After 2 h at 0° C. 81 mL of iodomethane (186 g, 1.32 mole) was added and the mixture was stirred for an additional 3 h, quenched with H₂O, concentrated and extracted with ether. The combined extracts were washed with brine, dried over MgSO₄, filtered and concentrated in vacuo to give an oily residue. Distillation afforded a mixture of (S)-carvone and product (bp 135–145° C., 70 Torr) that was separated by chromatography on silica gel using 39:1 hexanes-ethyl acetate to afford the title compound; ¹H NMR (CDCl₃) δ 1.06 (d, 3H, J=7 Hz), 1.72 (s, 3H), 1.79 (s, 3H), 4.82 (d, 2H, J=1.4 Hz).

Step 6: Preparation of S-6-(α)-Methyl-6-(β)-[5-methyl-3, 5-hexadienyl]carvone

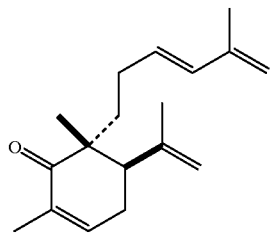

To a solution of 7.1 mL of diisopropylamine (5.2 g, 51 mmol) in 20 mL of dry THF at 0° C. was added 19 mL of n-butyllithium (2.5M, 47.6 mmol) in hexane. After stirring the mixture for 30 min, DMPU (5.8 mL, 47.6 mmol) and 6-methylcarvone (7.86 g, 48 mmol) were added. After 1h at 0° C., 7.6 g of 1-iodo-5-methyl-3,5-hexadiene (34 mmol) were added. The dark red solution was warmed to rt and stirred for an additional 14 h. The mixture was then diluted with 100 mL of hexanes, washed with brine, dried over MgSO₄, filtered and concentrated in vacuo. The residue was purified by chromatography on 500 g of silica gel using 39:1 hexanes-ether to afford the title compound; ¹H NMR (CDCl₃) δ 1.06 (s, 3H), 4.86 (s, 2H), 5.60 (m, 1H ), 6.24 (d, 1H, J=6 Hz), 6.57 (m, 1H).

Step 7: Preparation of [4b-S-4aα,4bβ,8aα,10aβ]-1-Oxo-2,4b,7,10a-tetramethyl-1,4,4a,4b,5,6,8a,9,10,10a-decahydro-1-[H]-phenanthrene

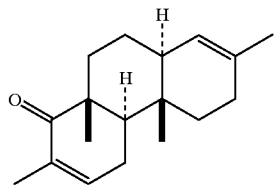

A solution of 1.91 g (7.4 mmol) of (S)-6-(α)-methyl-6-(β)-[5-methyl-3,5-hexadienyl]carvone and 100 mg (0.300 mmol, 0.04 eq.) of methylene blue in 160 mL of nonane was divided into 2 pressure tubes and sealed under argon. The solutions were stirred at 205–210° C. for 88 h, until tlc (silica gel, 1:1 toluene-hexane) indicated that reaction was almost complete. The solutions were combined and filtered though silica gel pad to remove methylene blue using EtOAc and filtrate was concentrated and purified by flash chromatography using 3:4 toluene-hexane to afford the title compound; ¹H NMR (CDCl₃)δ 0.85 (s, 3H), 1.07 (s, 3H), 1.08 (s, 3H), 1.09 (s, 3H), 6.67 (m, 1H).

Step 8: Preparation of [2-R-4aα,4bβ,8aα,10aβ]-2α-(1-R-hydroxyethyl)-1-oxo-2,4b,7,10a-tetramethyl-1,2,4a,4b,5,6,8a,9,10,10a-decahydro-1-[H]-phenanthrene

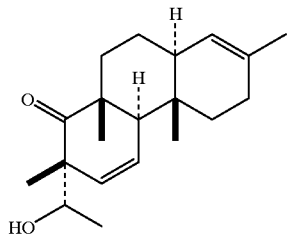

To a solution of 450 mg (1.74 mmol) of [4b-S-4aα,4bβ, 8aα,10aβ]-1-Oxo-2,4b,7,10a-tetramethyl-1,4,4a,4b,5,6,8a, 9,10,10a-decahydro-1-[H]-phenanthrene in 4 mL tetrahydrofuran was added 0.46 mL (3.84 mmol) of DMPU. The solution was cooled to −78° C. and 3.84 mL of a 1M solution of LHMDS in tetrahydrofuran was added. The solution was allowed to warm from −78° C. to −30° C. over 1.5 h, then was cooled to −78° C. Then 7.68 mL of a 0.5M solution of $ZnCl_2$ in ether was added, and after 10 minutes, 2 mL of freshly distilled acetaldehyde was added. The solution was stirred at −65° C. to −55° C. for 2 h, then warmed slowly to −30 ° C. over 3 h. The reaction was quenched by addition of 10 mL of aqueous $NH_4Cl$ and 10 mL of water. The layers were separated and the aqueous layer was washed with 3 portions of 50 mL ether. The combined extracts were washed with brine, dried over $MgSO_4$, and concentrated. The residue was purified by flash chromatography using 10% ether-hexane to afford the title compound; $^1H$ NMR ($CDCl_3$)δ 3.83 (m, 1H), 5.66 (m, 1H), 6.01 (d, 1H, J=3 Hz).

Step 9: Preparation of [2-R-4aα,4bβ,8aα,10aβ]-2α-(1-R-acetoxyethyl)-1-oxo-2,4b,7,10a-tetramethyl-1,2,4a,4b,5,6,8a,9,10,10a-decahydro-1-[H]-phenanthrene

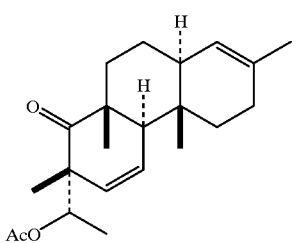

To a solution of 83 mg of [2-R-4aα,4bβ,8aα,10aβ]-2α-(1-R-hydroxyethyl)-1-oxo-2,4b,7,10a-tetramethyl-1,2,4a,4b,5,6,8a,9,10,10a-decahydro-1-[H]-phenanthrene in 0.5 mL of dichloromethane, and 50 mg of 4-dimethylaminopyridine (0.41 mmol, 1.5 eq) was added 0.13 mL of acetic anhydride (1.18 mmol, 5 eq). The mixture was stirred for 12 h, then poured into 5 mL of sat. aq. $NaHCO_3$ solution and extracted with ether. The combined organic extracts were washed with brine, dried over $MgSO_4$, filtered and concentrated. The residue was filtered though a plug of silica gel using 4:1 hexanes-ethyl acetate and purified by HPLC (Waters RCM, Prep Nova-Pak H Silica, 2 25×100 mmm cartridges) using a mixture of 1:9 methyl tert-butyl ether-hexane to afford the title compound; $^1H$ NMR ($CDCl_3$)δ 2.04 (s, 3H), 5.20 (m, 1H), 5.70 (m, 1H), 6.08 (d, 1H, J=3 Hz); 2.04 (s, 3H).

EXAMPLE 6

[1-S-3α,4α,4aα,4bβ,7α,8aα,10aβ]-2α-(1-R-acetoxyethyl)-8-(2-S-(2-ethylphenyl)propyl)-3,4-diacetoxy-1,8β-dihydroxy-2β,4b,7,10a-tetramethyl-1,2,3,4,4a,4b,5,6,7,8,8a,9,10,10a-tetradecahydro-2-[H]-phenanthrene

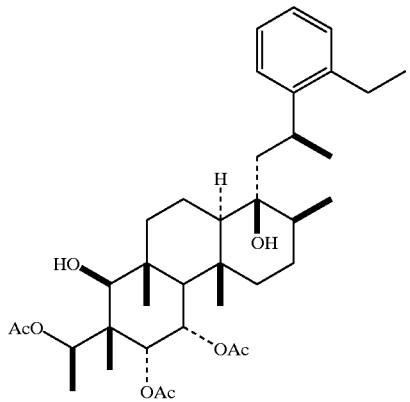

Step 1: Preparation of [2-R-4aα,4bβ,7α,8aβ,10aβ]-2α-(1-R-acetoxyethyl)-7,8 dihydroxy-1-oxo-2,4b,7,10a-tetramethyl-1,2,4a,4b,5,6,8a,9,10,10a-decahydro-1-[H]-phenanthrene

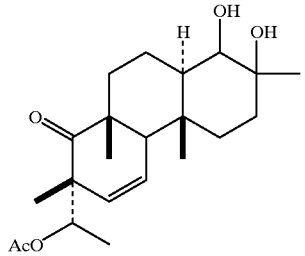

To a solution of 1.90 g (5.52 mmol) of [2-R-4aα,4bβ,7α,8aβ,10aβ]-2α-(1-R-acetoxyethyl)-1-oxo-2,4b,7,10a-tetramethyl-1,2,4a,4b,5,6,8a,9,10,10a-decahydro-1-[H]-phenanthrene in 20 mL of THF and 2.2 mL of water was added 561 mg (2.2 mmol) of $OsO_4$ and 6.46 g (55.2 mmol) of NMO (4-methylmorpholine-N-oxide). The reaction mixture was stirred for 26 h at rt. Then 50 mL of aqueous $NaHSO_4$ was added and the reaction mixture was stirred for 2.5 h. The reaction mixture was poured into 100 mL of ether. The water layer was extracted with methylene chloride (150 mL×4). The combined organic layer was dried over $MgSO_4$, filtered and concentrated to afford the title compound;

$^1H$ NMR ($CDCl_3$)δ 0.91(s, 3H), 1.57 (s, 3H), 2.05 (s, 3H), 5.21 (m, 1H), 5.73 (d, 1H, J=12 Hz), 6.00 (m, 1H);

Step 2: Preparation of [2-R-4aα,4bβ,7α,8aα,10aβ]-2α-(1-R-acetoxyethyl)-1,8-dioxo-2,4b,7,10a-tetramethyl-1,2,4a,4b,5,6,8a,9,10,10a-dodecahydro-1-[H]-phenanthrene

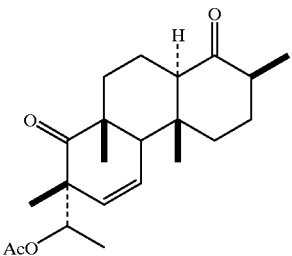

A solution of 2.08 g (5.51 mmol) of [2-R-4aα,4bβ,7α,8aβ,10aβ]-2α-(1-R-acetoxyethyl)-7,8 dihydroxy-1-oxo-2,4b,7,10a-tetramethyl-1,2,4a,4b,5,6,8a,9,10,10a-dodecahydro-1-[H]-phenanthrene and 838 mg (4.41 mmol) of TsOH.H₂O in 80 mL of toluene was stirred for 7 h at 80° C. It was then was concentrated and purified by silica gel chromatography with hexane/ether=500:85 to afford the title compound; ¹H NMR (CDCl₃)δ 0.82 (s, 3H), 1.02 (d, 3H, J=6 Hz), 1.11 (d, 3H, J=6 Hz), 1.13 (s, 3H), 2.06 (s, 3H), 5.20 (m, 1H), 5.77 (d, 1H, J=12 Hz), 6.01 (d, 1H, J=12 Hz);

Step 3: Preparation of (R)-2-(2-ethyl-phenyl)-propylbromide

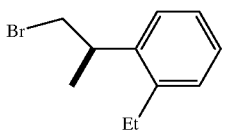

Step 3A: Preparation of 2-ethylphenylacetaldehyde

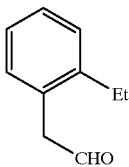

To a suspension of 8.53 g (350 mmol) of magnesium in 270 mL of dry THF was added 50 g (270 mmol) of 1-bromo-2-ethyl benzene. The temperature was maintained at 50° C. during addition, then was heated under reflux. After 1 h, the solution was cooled to −78° C. under N₂, and 54.42 g (324 mmol) of allyl iodide was added dropwise. The mixture was allowed to warm to room temperature, stirred for an additional 2 h, then cooled to 0° C. The reaction was quenched by addition of 2M HCl and 500 mL of ether and the layers were separated. The organic layer was washed with 30 mL of saturated NaHCO₃ solution and brine, dried over MgSO₄, filtered and concentrated. The oily residue was filtered through silica gel with 20% ethyl acetate-hexane and the eluate was concentrated to afford the crude 1-allyl-2-ethylbenzene as a colorless oil.

A solution of 54.05 g of the crude 1-allyl-2-ethylbenzene in 500 mL of 1:1 CH₂Cl₂—CH₃OH was cooled to −78° C. A stream of O₃ was bubbled through the solution for 3 h, untill all of the starting material had disappeared. Then a stream of air was bubbled through the solution until the blue color had faded. A total of 25 mL of methyl sulfide was added and the solution was stirred at room temperature for 1 h. The solution was concentrated and dried under vacuum to afford the title compound as a colorless oil which was used directly in Step 3B.

Step 3B: Preparation of (2-ethylphenyl)acetic acid

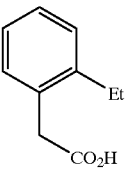

To a solution of the crude (2-ethylphenyl)acetaldehyde in 20 mL of EtOH was added a solution of 2.29 g (13.52 mmol) of AgNO₃ in 7.5 mL of water and a solution of 2.08 g (37.2 mmol) of KOH in 13 mL of water at 0° C. The reaction mixture was stirred at 0° C. for 2 h and was filtered to remove the solid. The filtrate was extracted with CH₂Cl₂ (20 mL×3) to remove impurities. The aqueous fraction was acidified with 6N HCl to pH=1 and this mixture was extracted with CH₂Cl₂ (50 mL×3). The combined organic layers were dried MgSO₄ and concentrated to give the title compound.

Step 3C: Preparation of (R)-4-benzyl-3-[2-(2-ethylphenyl)ethyl]-oxazolidin-2-one

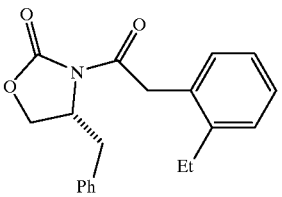

To a solution of 2.16 g (13.2 mmol) of (2-ethylphenyl) acetic acid and 1.6 g (15.84 mmol) of triethylamine in 55 mL of anhydrous THF was added 1.67 g (13.86 mmol) trimethylacetyl chloride at −78° C. under N₂. After the white suspension was stirred for 10 min at −78° C. and 30 min at 0° C., it was recooled to −78° C. and a −78° C. solution of metallated oxazolidinone prepared by the addition of 8.67 mL (13,86 mmol, 1.6 M in hexane) of n-butyllithium to a −78° C. solution of 2.46 g (13.86 mmol) of (R)-(+)-4-benzyl-2-oxazolidinone in 50 mL of anhydrous tetrahydrofuran was added via canula. The reaction mixture was stirred at 0° C. for an additional 30 min and quenched by the addition of 50 mL of saturated aqueous NH₄Cl. The two layers were separated and the aqueous layer was extracted with CH₂Cl₂ (50 mL×3). The combined organic layers were dried over MgSO₄, filtered and concentrated. The residue was purified by silica gel chromatography (6:1 hexane/ethyl acetate) to afford the title compound.

Step 3D: Preparation of (R),(R)-4-benzyl-3-[2-(2-ethyl-phenyl)-propyl]-oxazolidin-2-one

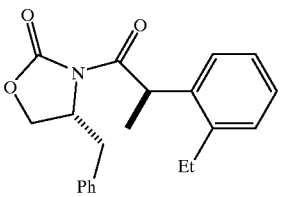

To a solution of 3.50 g (10.83 mmol) of (4R)-4-benzyl-3-[2-(2-ethyl-phenyl)-ethyl]-oxazolidin-2-one in 25 mL of THF was added a solution of 13 mL (1.0 M, 13 mmol) of sodium bis(tri-methylsilyl)amide at 78° C. under N₂. After the reaction mixture was stirred at −78° C. for 30 min, 3.29 g (9.92 mmol) of iodomethane was added at −78° C. The solution was stirred for 4 h and then quenched by the addition of 20 mL of aqueous saturated NH₄Cl solution. The two layers were separated and the aqueous was extracted with CH₂Cl₂ (50 mL×3). The combined organic layers were dried over MgSO₄, filtered and concentrated. The residue was purified by silica gel chromatography (500:35 hexane/ethyl acetate) to afford the title compound. $[\alpha]^P$=−146 (c=1.55, CHCl₃).

Step 3E: Preparation of (R)-2-(2-ethyl-phenyl)-propanol

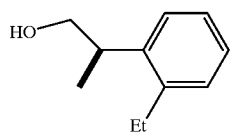

To a solution of 2.20 g (6.50 mmol) of (R),(R)-4-benzyl-3-[2-(2-ethyl-phenyl)-propyl]-oxazolidin-2-one in 20 mL of THF was added 13 mL (1.0 M in THF, 13 mmol) of LiAlH₄ slowly at 0° C. The reaction mixture was stirred at 0° C. for 2 h, then quenched by addition of 5 mL of water. The mixture was acidified with 2N HCl to PH=1 and was extracted with CH₂Cl₂ (50 mL×3). The combined organic layers were dried MgSO₄ and concentrated. The residue was purified by silica gel chromatography with 10:1 hexane/ethyl acetate to afford the title compound. $[\alpha]^P$=5.6 (c=7.15, CHCl₃).

Step 3F: Preparation of (R)-2-(2-ethyl-phenyl)-propylbromide

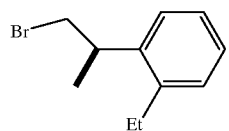

A solution of 0.93 g (6.20 mmol) of (R)-2-(2-ethyl-phenyl)-propanol and 2.60 g (9.92 mmol) of triphenylphosphine and 3.29 g (9.92 mmol) of carbon tetrabromide in 40 mL of ether was stirred at rt for 3 h. It was filtered and concentrated. The residue was purified by silica gel chromatography with hexane to afford the title compound as a colorless oil. $[\alpha]^P$=19.1 (c=1.15, CHCl₃).

Step 4: Preparation of [2-R-4aα,4bβ,7α,8aα,10aβ]-2α-(1-R-acetoxyethyl)-8-(2-S-(2-ethylphenyl)propyl)-8β-hydroxy-1-oxo-2β,4b,7,10a-tetramethyl-1,2,4a,4b,5,6,7,8,8a,9,10,10a-tetradecahydro-2-[H]-phenanthrene

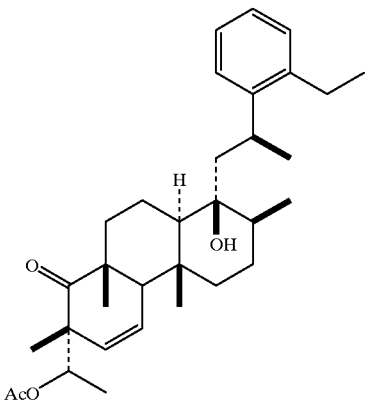

To a solution of [2-R-4aα,4bβ,7β,8aα,10aβ]-2α-(1-R-acetoxyethyl)-1,8-dioxo-2,4b,7,10a-tetramethyl-1,2,4a,4b,5,6,8a,9,10,10a-dodecahydro-1-[H]-phenanthrene (70.7 mg, 0.20 mmol) in 4.0 mL of THF was added the Grignard reagent (0.98 mmol, 2.45 mL as a 0.4 M solution)[prepared from (R)-2-(2-ethyl-phenyl)-propylbromide (Step 3) and 25 mg (1 mmol) magnesium) at 0° C. After 0.5 h, it was allowed to warm to rt for 4.5 h. The solution was diluted with CH₂Cl₂ and was quenched with 8 drops of pH=7 buffer. The cloudy solution was filtered though a plug of silica gel and was purified by HPLC (Waters RCM 25×10 silica gel, 1:4:5, CH₃CN:methyl t-butyl ether:hexanes) to give the title compound; ¹H NMR (CDCl₃)δ 7.28 (d, 1H, J=6.9 Hz), 7.16 (d of d, 1H, J 7.6, 1.6 Hz), 7.10 (d, 1H, J=7.8 Hz), 5.96 (d of d, 1H, J=10.3, 2.6 Hz), 5.65 (d of d, 1H, J=10.3, 3.2 Hz), 5.18 (q, 1H, J=6.2 Hz), 2.05 (s, 3H).

Part 5: Preparation of [1-S-4aα,4bβ,7β,8aα,10aβ]-2α-(1-R-hydroxyethyl)-8-(2-S-(2-ethylphenyl)propyl)-1,8β-dihydroxy-2β,4b,7,10a-tetramethyl-1,2,4a,4b,5,6,7,8,8a,9,10,10a-tetradecahydro-2-[H]-phenanthrene

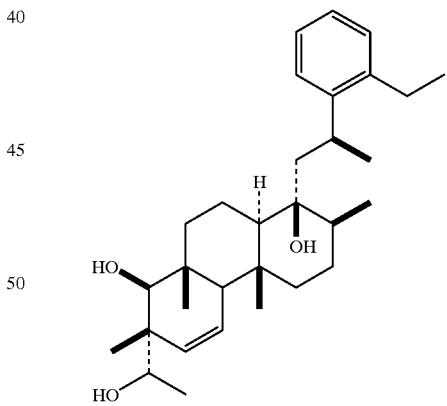

To a solution of [2-R-4aα,4bβ,7β,8aα,10aβ]-2α-(1-R-acetoxyethyl)-8-(2-S-(2-ethylphenyl)propyl)-8β-hydroxy-1-oxo-2β,4b,7,10a-tetramethyl-1,2,4a,4b,5,6,7,8,8a,9,10,10a-tetradecahydro-2-[H]-phenanthrene (57.9 mg, 0.11 mmol) in 2.0 mL of THF at −78° C. was added LiAlH₄ (0.55 mmol, as a 1 M solution in THF) and the reaction mixture was stirred at −78° C. for 3.8 h. It was then diluted with CH₂Cl₂ and quenched with pH=7 buffer (5 drops). The cloudy solution was filtered though a plug of silica gel and was purified by HPLC (Waters RCM 25×10 silica gel, 1:4:5, CH₃CN: methyl t-butyl ether: hexanes) to give the title compound; ¹H NMR (CDCl₃)δ 7.30 (d, 1H, J=7.4 Hz), 7.12–7.21 (m, 3H), 5.67 (d of d, 1H, J=10.1, 1.6 Hz), 5.36 (d of d, 1H, J=10.1, 3.0 Hz), 3.49 (q, 1H, J=6.4 Hz), 3.34 (d, 1H, J=3.5 Hz).

Step 5: Preparation of [1-S-4aα,4bβ,7β,8aα,10aβ]-2α-(1-R-hydroxyethyl)-8-(2-S-(2-ethylphenyl)propyl)-1,8β-dihydroxy-2β,4b,7,10a-tetramethyl-1,2,4a,4b,5,6,7,8,8a,9,10,10a-tetradecahydro-2-[H]-phenanthrene dimethylketal

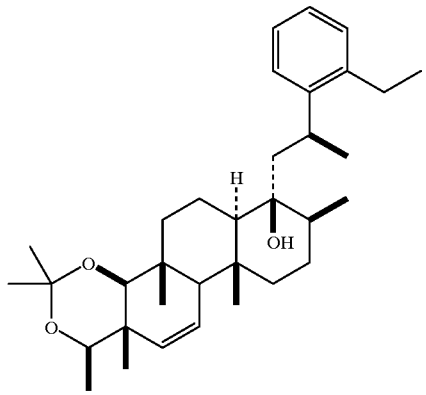

A solution of [1-S-4aα,4bβ,7β,8aα,10aβ]-2α-(1-R-hydroxyethyl)-8-(2-S-(2-ethylphenyl)propyl)-1,8β-dihydroxy-2β,4b,7,10a-tetramethyl-1,2,4a,4b,5,6,7,8,8a,9,10,10a-tetradecahydro-2-[H]-phenanthrene (29.2 mg, 0.062 mmol) in 1.5 mL of DMF was added 2,2-dimethoxypropane (0.5 mL, 4.1 mmol) and pyridium p-toluenesulfonate (2 mg, 0.008 mmol) at rt and the reaction mixture was stirred at rt for 1 h. The volatiles were removed by vacuum and the residue was purified by flash chromatography (silica, EtOAc/hexanes, 1:6) to give the title compound; ¹H NMR (CDCl₃)δ 7.30 (d, 1H, J=7.5 Hz), 7.19 (t, 1H, J=6.9 Hz), 7.08–7.13 (m, 2H), 5.59 (d, 1H, J=10.4 Hz), 5.41 (d of d, 1H, J=10.4, 3.2 Hz), 3.75 (q, 1H, J=6.2 Hz), 3.33 (s, 1H), 1.43 (s, 3H), 1.38 (s, 3H).

Step 6: Preparation of [1-S-3α,4α,4aα,4bβ,7β,8aα,10aβ]-2α-(1-R-hydroxyethyl)-8-(2-S-(2-ethylphenyl)propyl)-1,3,4,8β-tetrahydroxy-2β,4b,7,10a-tetramethyl-1,2,3,4,4a,4b,5,6,7,8,8a,9,10,10a-tetradecahydro-2-[H]-phenanthrene dimethylketal

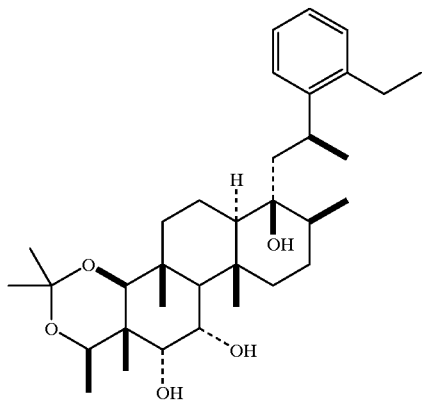

To a solution of [1-S-4aα,4bβ,7β,8aα,10aβ]-2α-(1-R-hydroxyethyl)-8-(2-S-(2-ethylphenyl)propyl)-1,8β-dihydroxy-2β,4b,7,10a-tetramethyl-1,2,4a,4b,5,6,7,8,8a,9,10,10a-tetradecahydro-2-[H]-phenanthrene, dimethylketal (27.4 mg, 0.052 mmol) in 1.0 mL of THF was added 0.5 mL of pyridine, 0.5 mL of water and OsO₄ (26.7 mg, 0.11 mmol) at rt and the reaction mixture was stirred at rt for 19 h. The reaction mixture was concentrated and the residue was redissolved in 10 mL of THF and 1 mL of water and the brown solution was bubbled with H₂S for 5 min. The solution was then filtered through a plug of silica gel and was dried to give the title compound; ¹H NMR (CDCl₃)δ 7.29 (d, 1H, J=7.6 Hz), 7.15–7.19 (m, 2H), 7.09 (t, 1H, J=7.1 Hz), 4.21 (q, 1H, J=6.2 Hz), 4.13 (d, 1H, J=10.2, 2.5 Hz), 3.47 (d, 1H, J=2.5 Hz), 3.21 (s, 1H), 1.44 (s, 6H).

Step 7: Preparation of [1-S-3α,4α,4aα,4bβ,7β,8aα,10aβ]-2α-(1-R-hydroxyethyl)-8-(2-S-(2-ethylphenyl)propyl)-3,4-diacetoxy-1,8β-dihydroxy-2β,4b,7,10a-tetramethyl-1,2,3,4,4a,4b,5,6,7,8,8a,9,10,10a-tetradecahydro-2-[H]-phenanthrene dimethylketal

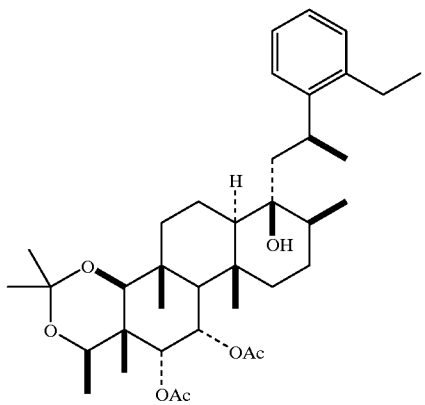

To a solution of [1-S-3α,4α,4aα,4bβ,7β, 8aα,10aβ]-2α-(1-R-hydroxyethyl)-8-(2-S-(2-ethylphenyl)propyl)-1,3,4,8,-tetrahydroxy-2β,4b,7,10a-tetramethyl-1,2,3,4,4a,4b,5,6,7,8,8a,9,10,10a-tetradecahydro-2-[H]-phenanthrene, dimethylketal (32.4 mg, 0.052 mmol) in 1.0 mL of THF was added pyridine (0.29 mL, 3.6 mmol), DMAP (2.9 mg, 0.024 mmol) and Ac₂O (0.16 mL, 1.6 mmol) at rt, and the reaction mixture was stirred at rt for 5 h. The volatiles were removed by vacuum and the residue purified by flash chromatography (silica, EtOAc/hexanes, 1:6) to give the title compound. ¹H NMR (CDCl₃)δ 7.31 (d, 1H, J=7.5 Hz), 7.17– 7.20 (m, 2H), 7.10 (t, 1H, J=7.2 Hz), 5.35 (d of d, 1H, J=11.9, 2.5 Hz), 4.95 (d, 1H, J=2.5 Hz), 3.88 (q, 1H, J=6.4 Hz), 2.13 (s, 3H), 1.91 (s, 3H0, 1.40 (s, 3H), 1.33 (s, 3H); MS (APCI) 644 (M+NH₄).

Step 8: Preparation of [1-S-3α,4α,4aα,4bβ,7β,8aα,10aβ]-2α-(1-R-hydroxyethyl)-8-(2-S-(2-ethylphenyl)propyl)-3,4-diacetoxy-1,8β-dihydroxy-2β,4b,7,10a-tetramethyl-1,2,3,4,4,4a,4b,5,6,7,8,8a,9,10,10a-tetradecahydro-2-[H]-phenanthrene

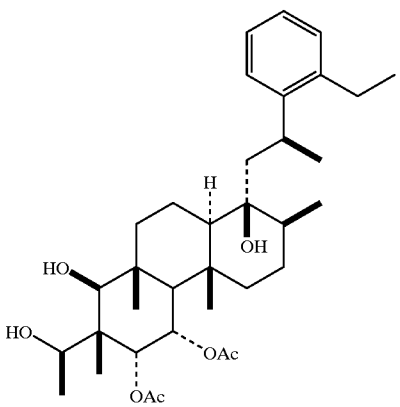

A solution of [1-S-3α,4α,4aα,4bβ,7β,8aβ,10aβ]-2α-(1-R-hydroxyethyl)-8-(2-S-(2-ethylphenyl)propyl)-3,4-diacetoxy-1,8,β-dihydroxy-2β,4b,7,10a-tetramethyl-1,2,3,4,4a,4b,5,6,7,8,8a,9,10,10a-tetradecahydro-2-[H]-phenanthrene, dimethylketal (11.2 mg, 0.018 mmol) and p-toluenesulfonic acid (2.2 mg, 0.012 mmol) in 4.0 mL of MeOH was stirred at 45° C. for 3.6 h. The volatiles were removed by vacuum and the residue purified by chromatography (silica, EtOAc/hexanes, 3:7) to give the title compound; $^1$H NMR (CDCl$_3$)δ 7.13–7.30 (m, 4H), 5.38 (d of d, 1H, J=11.7, 2.3 Hz), 4.92 (s, 1H), 3.97 (q, 1H, J=6.1 Hz), 2.10 (s, 3H), 1.95 (s, 3H).

Step 9: Preparation of [1-S-3α,4α,4aα,4bβ,7β,8aα,10aβ]-2α-(1-R-acetoxyethyl)-8-(2-S-(2-ethylphenyl)propyl)-1,3,4-triacetoxy-8β-hydroxy-2β,4b,7,10a-tetramethyl-1,2,3,4,4a,4b,5,6,7,8,8a,9,10,10a-tetradecahydro-2-[H]-phenanthrene

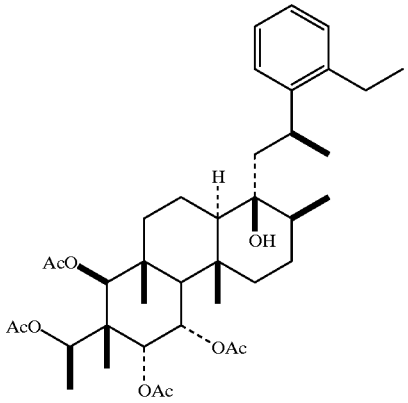

A solution of [1-S-3α,4α,4aα,4bβ,7β,8aα,10aβ-2α-(1-R-hydroxyethyl)-8-(2-S-(2-ethylphenyl)propyl)-3,4-diacetoxy-1,8β-dihydroxy-2β,4b,7,10a-tetramethyl-1,2,3,4,4a,4b,5,6,7,8,8a,9,10,10a-tetradecahydro-2-[H]-phenanthrene (15.1 mg, 0.026 mmol) in 2.0 mL of THF, pyridine (0.20 mL, 2.5 mmol), DMAP (2.3 mg, 0.019 mmol) and Ac$_2$O (0.16 mL, 1.6 mmol) was stirred at rt for 17.5 h. The volatiles were removed by vacuum and the residue purified by HPLC (Waters RCM 25×10 silica gel, 1:4:5, CH$_3$CN: methyl t-butyl ether: hexanes) to afford the title compound; $^1$H NMR (CDCl$_3$)δ 7.15–7.28 (m, 4H), 5.38 (d of d, 1H, J=10.3, 2.8 Hz), 6.16 (bs, 1H), 4.97 (bs, 1H), 4.68 (s, 1H), 2.10 (s, 3H), 2.05 (s, 3H), 2.03 (s, 3H), 1.99 (s, 3H).

Step 10: Preparation of [1-S-3α,4α,4aα,4bβ,7β,8aα,10aβ]-2α-(1-R-acetoxyethyl)-8-(2-S-(2-ethylphenyl)propyl)-3,4-diacetoxy-1,8β-dihydroxy-2β,4b,7,10a-tetramethyl-1,2,3,4,4a,4b,5,6,7,8,8a,9, 10,10a-tetradecahydro-2-[H]-phenanthrene

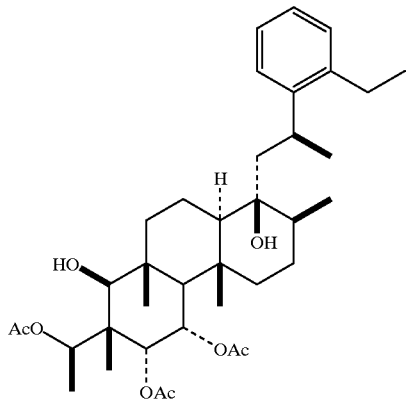

Further elution of the column in Step 8 afforded the title compound: $^1$H NMR (CDCl$_3$)δ 7.13–7.29 (m, 4H), 5.37 (d of, 1H, J=11.5, 2.8 Hz), 5.03 (d, 1H, J=2.5 Hz), 5.00 (q, 1H, J=6.4 Hz), 2.12 (s, 3H), 2.06 (s, 3H), 1.97 (s, 3H); MS (APCI) 646 (M+NH$_4$)

EXAMPLE 7

Preparation of [1-S-3α,4α,4aα,4bβ,7β,8aα,10aβ]-2α-(1-R-acetoxyethyl)8-(2-S-(2-ethylphenyl)propyl)-3,4-diacetoxy-8β-hydroxy-1-oxo-2b,4b,7,10a-tetramethyl-1,2,3,4,4a,4b,5,6,7,8,8a,9,10,10a-tetradecahydro-2-[H]-phenanthrene

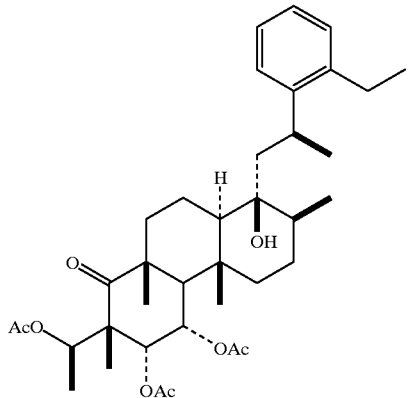

A solution of [1-S-3α,4α,4aα,4bβ,7β,8aα,10aβ-2α-(1-R-acetoxyethyl)-8-(2-S-(2-ethylphenyl)propyl)-3,4-diacetoxy-1,8β-dihydroxy-2β,4b,7,10a-tetramethyl-1,2,3,4,4a,4b,5,6,7,8,8a,9,10,10a-tetradecahydro-2-[H]-phenanthrene (5.1 mg, 0.008 mmol), PDC (pyridinium dichromate) (112 mg, 0.29 mmol) in 2.0 mL of CH$_2$Cl$_2$ was stirred at rt for 80 h. It was then filtered though a plug of silica gel and the residue purified by HPLC (Waters RCM 25×10 silica gel, 1:4:5, CH$_3$CN: methyl t-butyl ether: hexanes) to give the title compound. $^1$H NMR (CDCl$_3$)δ 7.13–7.28 (m, 4H), 5.49–5.51 (m, 2H), 5.40 (q, 1H, J=6.4 Hz), 2.03 (bs, 6H), 2.02 (s, 3H); MS (APCI) 644 (M 30 NH$_4$).

What is claimed is:

1. A compound of structural Formula I:

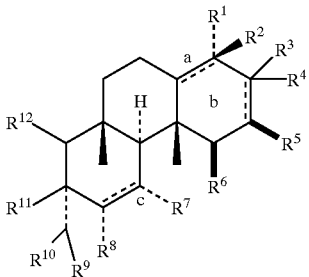

I or a pharmaceutically acceptable salt, crystal form, or hydrate thereof, wherein:
a, b and c are independently a single bond or a double bond, and represented by === in the structure above;
n is: 0, 1 or 2;
r is: 0 or 1;
s is: 0 or 1;
$R^1$ and $R^2$ are independently:
  (1) hydroxyl,
  (2) ($C_1$–$C_6$)-alkyloxy,
  (3) H,
  (4) OCO($C_1$–$C_6$)-alkyl,
  (5) ($C_1$–$C_6$)-alkyl,
  (6) $R^1$ and $R^2$ taken together is an exo-methylene group,
  (7) $R^1$ and $R^2$ taken together is =O,
  (8) ($C_1$–$C_6$)-alkylaryl, wherein aryl is as defined in $R^{11}$ below, or
  (9) ($C_2$–$C_8$)alkenyl;
with the proviso that $R^2$ is absent when a is a double bond;
$R^3$ and $R^4$ are independently:
  (1) hydroxyl,
  (2) ($C_1$–$C_6$)-alkyloxy,
  (3) H,
  (4) OCO($C_1$–$C_6$)-alkyl,
  (5) ($C_1$–$C_6$)-alkyl,
  (6) phenyl,
  (7) $R^3$ and $R^5$ taken together is an oxirane group when b is a single bond, or
  (8) $(CH_2)_n$aryl, wherein aryl is as defined below;
with the proviso that $R^4$ is absent when b is a double bond, additionally, $R^3$ and $R^4$ can be taken together to be =O when b is a single bond;
$R^5$, $R^6$, $R^7$ and $R^8$ are independently selected from the group consisting of:
  (1) $O[(C=O)O_r]_s R^{13}$,
  (2) $O[(C=O)O_r]_s$-aryl, aryl as defined below,
  (3) $O[(C=O)O_r]_s$-heteroaryl,
  (4) hydrogen, provided that $R^5$, $R^6$, $R^7$ and $R^8$ are not all hydrogen at the same time when c is a single bond,
  (5) ($C_1$–$C_6$)alkylaryl, wherein aryl is as defined below, and
  (6) hydroxyl;
$R^9$ is:
  (1) H,
  (2) OH,
  (3) =O,
  (4) $O[(C=O)O_r]_s$($C_1$–$C_6$)-alkyl, alkyl as defined below,
  (5) $O[(C=O)O_r]_s$($C_2$–$C_6$)-alkenyl, as defined below,
  (6) $O[(C=O)O_r]_s$-aryl, aryl as defined below,
  (7) $O[(C=O)O_r]_s$-heteroaryl,
  (8) $O(CH_2)_n$-heteroaryl,
  (9) $O(CH_2)_n$-aryl, aryl as defined below, or
  (10) $R^9$ and $R^{12}$ are connected to form

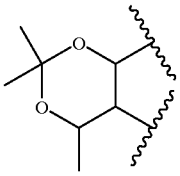

when $R^{10}$ is methyl and $R^{11}$ is H;
$R^{10}$ is:
  (1) $CH_3$, or
  (2) H;
$R^{11}$ is chosen from the group consisting of:
  (1) H,
  (2) ($C_1$–$C_6$)-alkyl, wherein alkyl is unsubstituted or substituted with one or two of the substituents selected from the group consisting of:
    (a) halo, wherein halo is fluoro, chloro, bromo, or iodo,
    (b) hydroxy,
    (c) oxo,
    (d) ($C_1$–$C_6$)-alkyloxy,
    (e) ($C_1$–$C_6$)-alkyl—$S(O)_n$—,
    (f) aryl-($C_1$–$C_6$)-alkyloxy, wherein aryl is defined as phenyl or naphthyl, unsubstituted or substituted with one, two or three of the substituents selected from the group consisting of:
      (a') halo, wherein halo is fluoro, chloro, bromo, or iodo,
      (b') hydroxy,
      (c') ($C_1$–$C_6$)-alkyl,
      (d') ($C_1$–$C_4$)-perfluoroalkyl,
      (e') ($C_1$–$C_6$)-alkenyl,
      (f') ($C_1$–$C_6$)-alkynyl,
      (g') ($C_1$–$C_6$)-alkyloxy,
      (h') ($C_1$–$C_6$)-alkyl—$S(O)_n$—,
      (i') phenyl,
      (j') phenoxy,
      (k') cyano,
      (l') nitro,
      (m') $CO_2H$,
      (n') CO($C_1$–$C_6$)-alkyl,
      (o') $CO_2$($C_1$–$C_6$)-alkyl,
      (p') $CONR^{13}R^{14}$,
      (q') $NR^{13}R^{14}$,
      (r') $NR^{13}CO$($C_1$–$C_6$)-alkyl,
      (s') ($C_1$–$C_6$)-alkenyloxy, and
      (t') benzyloxy;
    (g) cyano,
    (h) nitro,
    (i) vinyl,
    (j) $NR^{13}R^{14}$,
    (k) $NR^{13}CO$($C_1$–$C_6$)-alkyl,
    (l) CHO,
    (m) $CO_2H$,
    (n) CO($C_1$–$C_6$)-alkyl,
    (o) $CO_2$($C_1$–$C_6$)-alkyl,
    (p) $CONR^{13}R^{14}$,
    (q) aryl, wherein aryl is as defined above,
    (r) $OCOCH_3$, and
    (s) $(CH_2)_n O(CO)CH(SPh)_2$;
  (3) ($C_2$–$C_6$)-alkenyl, wherein alkenyl is unsubstituted or substituted with one or two of the substituents selected from the group consisting of:

(a) halo, wherein halo is fluoro, chloro, bromo, or iodo,
(b) hydroxy,
(c) oxo,
(d) $(C_1-C_6)$-alkyloxy,
(e) $(C_1-C_6)$-alkyl—S(O)$_n$—,
(f) phenyl-$(C_1-C_6)$-alkyloxy,
(g) cyano,
(h) nitro,
(i) vinyl,
(j) $NR^{13}R^{14}$,
(k) $NR^{13}CO(C_1-C_6)$-alkyl,
(l) CHO,
(m) $CO_2H$,
(n) $CO(C_1-C_6)$-alkyl,
(o) $CO_2(C_1-C_6)$-alkyl,
(p) $CONR^{13}R^{14}$,
(q) aryl, wherein aryl is as defined above,
(r) heteroaryl, and
(s) $OCOCHC_3$,
(4) $(CH_2)_nO(C_2-C_6)$-alkenyl, wherein alkenyl is as defined above,
(5) CHO,
(6) COOH,
(7) $CONR^{13}R^{14}$,
(8) $O[(C=O)O_r]_s(C_1-C_6)$-alkyl, alkyl as defined above,
(9) $(CH_2)_nS(C_1-C_6)$-alkyl, wherein alkyl is as defined above,
(10) $(CH_2)_nS(C_2-C_6)$-alkenyl, wherein alkenyl is as defined above,
(11) $(CH_2)_nS$-aryl, wherein aryl is as defined above, or
(12) $(CO)(C_1-C_6)$-alkyl, wherein alkyl is as defined above;

$R^{12}$ is as defined above for $R^{11}$ or
(1) =O,
(2) =CH—$(C_1-C_6)$-alkyl, wherein alkyl is as defined above,
(3) =CH—$(C_1-C_6)$-alkenyl, wherein alkenyl is as defined above,
(4) =CH-aryl, wherein aryl is as defined above,
(5) hydroxyl, or
(6) $R^9$ and $R^{12}$ are connected to form

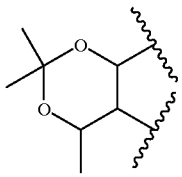

when $R^{10}$ is methyl; and $R^{11}$ is H;
$R^{13}$ and $R^{14}$ are independently:
(1) hydrogen,
(2) $(C_1-C_6)$-alkyl, or
(3) phenyl.

2. The compound of structural Formula I as recited in claim 1, wherein
$R^1$ and $R^2$ are independently:
(1) hydroxyl,
(2) $(C_1-C_6)$-alkyloxy,
(3) H,
(4) $(C_1-C_6)$-alkyl,
(5) $R^1$ and $R^2$ taken together is =O,
(6) $(C_1-C_6)$-alkylphenyl wherein the phenyl is unsubstituted or substituted with $(C_1-C_6)$alkyloxy, hydroxyl, or $(C_1-C_6)$alkyl, and alkyl is branched or unbranched, or
(7) $(C_2-C_8)$alkenyl;
with the proviso that $R^2$ is absent when a is a double bond;
$R^3$ and $R^4$ are independently:
(1) hydroxyl,
(2) $(C_1-C_6)$-alkyloxy,
(3) H,
(4) $OCO(C_1-C_6)$-alkyl,
(5) $(C_1-C_6)$-alkyl,
(6) phenyl,
(7) $R^3$ and $R^5$ taken together is an oxirane group when b is a single bond, or
(8) $(CH_2)_n$benzene, wherein the benzene is unsubstituted or substituted with hydroxyl or $(C_1-C_6)$-alkyloxy;
with the proviso that $R^4$ is absent when b is a double bond, and when b is a single bond $R^3$ and $R^4$ together are oxo,
$R^5, R^6, R^7$ and $R^8$ are independently selected from the group consisting of:
(1) $O[(C=O)O_r]_sR^{13}$,
(2) $O[(C=O)O_r]_s$-aryl,
(3) hydrogen, provided that $R^5, R^6, R^7$ and $R^8$ are not all hydrogen at the same when c is a single bond,
(4) $(C_1-C_6)$alkylbenzene, wherein the benzene is unsubstituted or substituted with $(C_1-C_6)$-alkyl and alkyl is branched or unbranched;
(5) hydroxyl;

R is:
(1) H.
(2) OH,
(3) =O,
(4) $O[(C=O)O_r]_s(C_1-C_6)$-alkyl, wherein alkyl is branched or unbranched, or
(5) $R^9$ and $R^{12}$ are connected to form

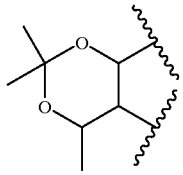

when $R^{10}$ is methyl; and $R^{11}$ is H;
$R^{10}$ is:
(1) $CH_3$, or
(2) H;
$R^{11}$ is chosen from the group consisting of:
(1) H,
(2) $(C_1-C_6)$alkyl, substituted with $(CH_2)_nO(CO)CH(SPh)_2$,
(3) $(CH_2)_nO(C_1-C_6)$alkyl,
(4) $(CO)(C_1-C_6)$-alkyl,
(5) $(C_1-C_6)$-alkyl, or
(6) CHO;
$R^{12}$ is as defined above for $R^{11}$ or
(1) =O,
(2) $O(CO)(C_1-C_6)$-alkyl,
(3) hydroxyl, or (4) $R^9$ and $R^{12}$ are connected to form

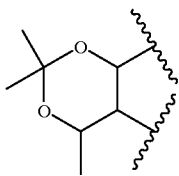

when $R^{10}$ is methyl; and $R^{11}$ is H;
$R^{13}$ is:
(1) hydrogen, or
(2) $(C_1-C_6)$-alkyl.

3. The compound of structural Formula I as recited in claim 2, wherein
$R^1$ and $R^2$ are independently:
(1) hydroxyl,
(2) H,
(3) $R^1$ and $R^2$ taken together is =O,
(4) $(C_1-C_3)$-alkylphenyl wherein the phenyl is unsubstituted or substituted with $(C_1-C_3)$alkyloxy, hydroxyl, or $(C_1-C_3)$alkyl, and alkyl is branched or unbranched, or
(5) $(C_2-C_8)$alkenyl;
with the proviso that $R^2$ is absent when a is a double bond;
$R^3$ and $R^4$ are independently:
(1) hydroxyl,
(2) $(C_1-C_3)$-alkyloxy,
(3) H,
(4) $(C_1-C_3)$-alkyl,
(5) $(CH_2)_n$benzene, wherein the benzene is unsubstituted or substituted with hydroxyl or $(C_1-C_3)$-alkyloxy;
with the proviso that $R^4$ is absent when b is a double bond, and when b is a single bond $R^3$ and $R^4$ together are oxo, $R^5, R^6, R^7$ and $R^8$ are independently selected from the group consisting of:
(1) $O(C=O)(C_1-C_3)$alkyl, >(2) hydrogen, provided that $R^5, R^6, R^7$ and $R^8$ are not all hydrogen at the same time when c is a single bond,
(3) $(C_1-C_3)$alkylbenzene, wherein the benzene is unsubstituted or substituted with $(C_1-C_3)$-alkyl and alkyl is branched or unbranched;
(4) $O(C_1-C_3)$alkyl, and
(5) hydroxyl;
$R^9$ is:
(1) H,
(2) OH,
(3) =O,
(4) $O(C=O)(C_1-C_3)$alkyl, or
(5) $R^9$ and $R^{12}$ are connected to form

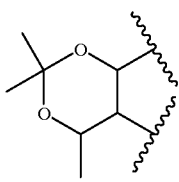

when $R^{10}$ is methyl and $R^{11}$ is H;
$R^{10}$ is:
(1) $CH_3$, or
(2) H;
$R^{11}$ is chosen from the group consisting of:

(1) H,
(2) $CH_2O(CO)CH(SPh)_2$,
(3) $CH_2O(C_1-C_3)$alkyl, and
(4) $(C_1-C_3)$-alkyl;
$R^{12}$ is:
(1) =O,
(2) $R^9$ and $R^{12}$ are connected to form

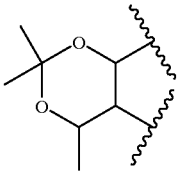

when $R^{10}$ is methyl and $R^{11}$ is H;
(3) CHO,
(4) $CH_2O(C_1-C_3)$alkyl,
(5) hydroxyl, or
(6) $O(CO)(C_1-C_3)$alkyl.

4. A compound selected from the group consisting of:
1β-S-2α,2β,3α,4α,3aα,4bβ,5β,8aα,10aβ]-2α-(1-R-acetoxyethyl)-2β-(2,2-diphenylthioacetoxymethyl)-1-formyl-8-oxo-2b,4b,7,10a-tetramethyl-3,4,5-triacetoxy-1,2,3,4,4a,4b,5,8,8a,9,10,10a-dodecahydro-2-[H]-phenanthrene,

[1β-S-2α,2β,3α,4α,3aα,4bβ,5β,8aα,10aβ]-2α-(1-R-acetoxyethyl)-2β-(2,2-diphenylthioacetoxymethyl)-1-formyl-8-(2-(2-methoxyphenyl)ethyl)-8-hydroxy-2b,4b,7,10a-tetramethyl-3,4,5-triacetoxy-1,2,3,4,4a,4b,5,8,8a,9,10,10a-dodecahydro-2-[H]-phenanthrene, 1β-S-2α,2β,3α,4α,3aα,4bβ,5β,8aα,10aβ]-2α-(1-R-acetoxyethyl)-1β,2β-bis(hydroxymethyl)-8-(2-(2-methoxyphenyl)ethyl)-8-hydroxy-2b,4b,7,10a-tetramethyl-3,4,5-triacetoxy-1,2,3,4,4a,4b,5,8,8a,9,10,10a-dodecahydro-2-[H]-phenanthrene, 1β-S-2α,2β,3α,4α,3aα,4bβ,5α,8aα,10aβ]-2α-(1-R-acetoxyethyl)-1β,2β-bis(methoxymethyl)-8-(2-(2-methoxyphenyl)ethyl)-8-hydroxy-2b,4b,7,10a-tetramethyl-3,4,5-triacetoxy-1,2,3,4,4a,4b,5,8,8a,9,10,10a-dodecahydro-2-[H]-phenanthrene, 4b-S-4aα,4bβ,8aα,10aβ]-2α-(1-R-acetoxyethyl)-2β-methyl-8-hydroxy-1-oxo-2,4b,7,10a-tetramethyl-1,2,4a,4b,5,6,8a,9,10,10a-decahydro-1-[H]-phenanthrene,

[1-S-3α,4α,4aα,4bβ,7β,8aα,10aβ]-2α-(1-R-acetoxyethyl)-8-(2-S-(2-ethylphenyl)propyl)-3,4-diacetoxy-1,8β-dihydroxy-2β,4b,7,10a -tetramethyl-1,2,3,4,4a,4b,5,6,7,8,8a,9,10,10a-tetradecahydro-2-[H]-phenanthrene,

[2-R-4aα,4bβ,7β,8aα,10aβ]-2α-(1-R-acetoxyethyl)-8-(2-S-(2-ethylphenyl)propyl)-8β-hydroxy-1-oxo-2β,4b,7,10a-tetramethyl-1,2,4a,4b,5,6,7,8,8a,9,10,10a-tetradecahydro-2-[H]-phenanthrene,

[1-S-3α,4α,4aα,4bβ,7β,8aα,10aβ]-2α-(1-R-hydroxyethyl)-8-(2-S-(2-ethylphenyl)propyl)-3,4-diacetoxy-1,8β-dihydroxy-2β,4b,7,10a-tetramethyl-1,2,3,4,4a,4b,5,6,7,8,8a,9,10,10a-tetradecahydro-2-[H]-phenanthrene, dimethylketal,

[1-S-3α,4α,4aα,4bβ,7β,8aα,10aβ]-2α-(1-R-acetoxyethyl)-8-(2-S-(2-ethylphenyl)propyl)-1,3,4-triacetoxy-8β-hydroxy-2β,4b,7,10a-tetramethyl-1,2,3,4,4a,4b,5,6,7,8,8a,9,10,10a-tetradecahydro-2-[H]-phenanthrene,

[1-S-3α,4α,4aα,4bβ,7β,8aα, 10aβ]-2α-(1-R-acetoxyethyl)-8-(2-S-(2-ethylphenyl)propyl)-3,4-diacetoxy-1,8β-dihydroxy-2β,4b,7,10a-tetramethyl-1,2,3,4,4a,4b,5,6,7,8,8a,9,10,10a-tetradecahydro-2-[H]-phenanthrene, and

[1-S-3α,4α,4aα,4bβ,7β,8aα,10aβ]-2α-(1-R-acetoxyethyl)-8-(2-S-(2-ethylphenyl)propyl)-3,4-diacetoxy-8β-hydroxy-1-oxo-2β,4b,7,10a-tetramethyl-1,2,3,4,4a,4b,5,6,7,8,8a,9,10,10a-tetradecahydro-2-[H]-phenanthrene or a pharmaceutically acceptable salt, crystal form or hydrate thereof.

5. A compound of structural Formula II

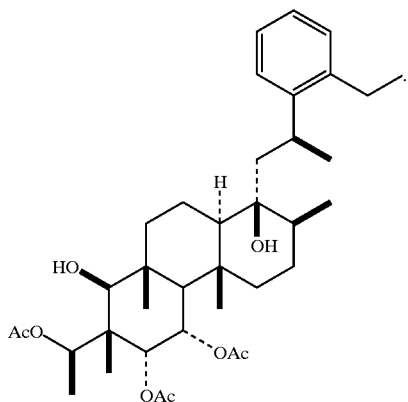

II

6. A compound of structural Formula III

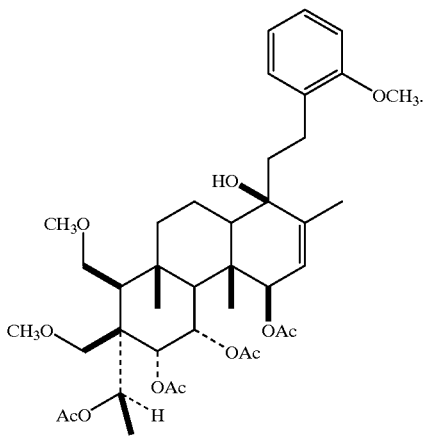

III

7. A method of treating a condition in a mammal, the treatment of which is effected or facilitated by $K_v1.3$ inhibition, comprising the administration, in an amount that is effective at inhibiting $K_v1.3$, of a compound of Formula I, as recited in claim 1.

8. A method of preventing or treating the resistance to transplantation or transplantation rejection of organs or tissues into a patient in need thereof, which comprises the administration of a compound of claim 1.

9. A method of suppressing the immune system in a subject in need thereof, which comprises the administration to the subject of an immune suppressing amount of a compound of Formula I, as recited in claim 1.

10. A pharmaceutical formulation comprising a pharmaceutically acceptable carrier and a therapeutically effective amount of the compound of Formula I, as recited in claim 1 or a pharmaceutically acceptable crystal form or hydrate thereof.

11. The pharmaceutical formulation of claim 10, comprising in addition, a second immunosuppressive compound which is selected from azathioprine, brequinar sodium, deoxyspergualin, mizaribine, mycophenolic acid morpholino ester, cyclosporin, FK-506 and rapamycin.

12. The method of claim 8, comprising the coadministration of a second immunosuppressive compound.

13. A method of preventing or treating the resistance to transplantation or transplantation rejection of organs or tissues into a patient in need thereof, which comprises the administration of a compound of claim 1.

14. A method of treating a condition in a mammal, the treatment of which is effected or facilitated by $K_v1.3$ inhibition, comprising the administration of a pharmaceutical formulation comprising a pharmaceutical carrier and a compound of Formula I, as recited in claim 1, in an amount that is effective at inhibiting $K_v1.3$.

15. A method of treating a condition in a mammal, the treatment of which is effected or facilitated by $K_v1.3$ inhibition, comprising the coadministration of a therapeutically effective amount of a compound of formula I, as recited in claim 1, with a second immunosuppressive agent.

16. The method of claim 12 wherein the second immunosuppressive compound is chosen from the group consisting of azathioprine, brequinar sodium, deoxyspergualin, mizaribine, mycophenolic acid morpholino ester, cyclosporin, FK-506 and rapamycin.

* * * * *